US010390895B2

United States Patent
Henderson et al.

(10) Patent No.: US 10,390,895 B2
(45) Date of Patent: Aug. 27, 2019

(54) CONTROL OF ADVANCEMENT RATE AND APPLICATION FORCE BASED ON MEASURED FORCES

(71) Applicant: Ethicon Endo-Surgery, LLC, Guaynabo, PR (US)

(72) Inventors: Cortney E. Henderson, Loveland, OH (US); Frederick E. Shelton, IV, Hillsboro, OH (US); Jason L. Harris, Lebanon, OH (US); David C. Yates, West Chester, OH (US); Tamara S. Widenhouse, Clarksville, OH (US)

(73) Assignee: Ethicon LLC, Guaynabo, PR (US)

( * ) Notice: Subject to any disclaimer, the term of this patent is extended or adjusted under 35 U.S.C. 154(b) by 256 days.

(21) Appl. No.: 15/237,753

(22) Filed: Aug. 16, 2016

(65) Prior Publication Data

US 2018/0049822 A1 Feb. 22, 2018

(51) Int. Cl.
*A61B 18/14* (2006.01)
*A61B 34/30* (2016.01)
(Continued)

(52) U.S. Cl.
CPC ...... *A61B 34/30* (2016.02); *A61B 17/320016* (2013.01); *A61B 34/76* (2016.02);
(Continued)

(58) Field of Classification Search
CPC ......... A61B 34/30; A61B 34/35; A61B 34/37; A61B 18/1442; A61B 2018/1455;
(Continued)

(56) References Cited

U.S. PATENT DOCUMENTS 6,184,868 B1 2/2001 Shahoian et al.
6,296,635 B1 * 10/2001 Smith ..................... B25J 3/04
606/1
(Continued)

FOREIGN PATENT DOCUMENTS

WO WO 2015094493 A1 * 6/2015 ......... A61B 18/1445

OTHER PUBLICATIONS

Correlated Solutions, "Principle of Digital Image Correlation," 2013 (http://correlatedsolutions.com/digital-image-correlation/).
(Continued)

*Primary Examiner* — Thomas A Giuliani
(74) *Attorney, Agent, or Firm* — Mintz Levin Cohn Ferris Glovsky and Popeo, P.C.

(57) ABSTRACT

A robotic surgical system including a control system that controls the movement of a robotic arm is described. The robotic arm can be coupled to a tool assembly that includes an end effector positioned at a distal end of a shaft. The control system can assist with controlling the movement of the end effector and any tooling (e.g., cutting tool, boring tool, jaws, etc.) associated with the end effector, such as for either cutting through tissue or controlling a tension in the tissue. The tool assembly can include one or more sensors that measure a variety of forces or velocities associated with either the robotic arm or end effector. The control system can collect and monitor such sensed forces and velocities to determine and control one or more appropriate movement parameters associated with the robotic arm thereby controlling the cutting of tissue and preventing unwanted cutting of tissue. Furthermore, movement parameters associated with more than one robotic arm can be controlled by the control system.

19 Claims, 20 Drawing Sheets

(51) Int. Cl.
  *A61B 34/00*  (2016.01)
  *A61B 17/32*  (2006.01)
  *A61B 17/00*  (2006.01)
  *A61B 17/34*  (2006.01)
  *A61B 90/00*  (2016.01)

(52) U.S. Cl.
  CPC ... *A61B 17/320068* (2013.01); *A61B 18/1402* (2013.01); *A61B 2017/00477* (2013.01); *A61B 2017/320052* (2013.01); *A61B 2017/3405* (2013.01); *A61B 2090/064* (2016.02)

(58) Field of Classification Search
  CPC ............ A61B 18/1445; A61B 18/1402; A61B 2018/1412; A61B 2018/1452; A61B 2018/00607; A61B 17/3211; A61B 17/320016; A61B 17/320068; A61B 2090/064; A61B 2017/00022; A61B 34/76; A61B 2034/302
  USPC .......... 606/41, 42, 45, 48–52, 130; 700/245; 318/568.11, 568.16; 901/6, 9, 30, 31, 901/34–39
  See application file for complete search history.

(56) References Cited

U.S. PATENT DOCUMENTS

| | | |
|---|---|---|
| 8,114,345 B2 | 2/2012 | Dlugos, Jr. et al. |
| 8,224,484 B2 | 7/2012 | Swarup et al. |
| 8,882,792 B2 | 11/2014 | Dietz et al. |
| 8,915,842 B2 | 12/2014 | Weisenburgh, II et al. |
| 8,931,682 B2 | 1/2015 | Timm et al. |
| 8,945,098 B2 | 2/2015 | Seibold et al. |
| 9,895,813 B2 | 2/2018 | Blumenkranz et al. |
| 2002/0062177 A1 | 5/2002 | Hannaford et al. |
| 2007/0078484 A1 | 4/2007 | Talarico et al. |
| 2007/0287992 A1* | 12/2007 | Diolaiti ................. G05B 19/19 606/1 |
| 2008/0046122 A1 | 2/2008 | Manzo et al. |
| 2008/0081948 A1 | 4/2008 | Weisenburgh et al. |
| 2008/0262525 A1 | 10/2008 | Chang et al. |
| 2009/0182436 A1 | 7/2009 | Ferrara |
| 2009/0216374 A1 | 8/2009 | Low et al. |
| 2009/0248037 A1 | 10/2009 | Prisco |
| 2009/0248038 A1 | 10/2009 | Blumenkranz et al. |
| 2011/0118709 A1 | 5/2011 | Burbank |
| 2011/0118778 A1 | 5/2011 | Burbank |
| 2011/0160745 A1 | 6/2011 | Fielding et al. |
| 2011/0201885 A1 | 8/2011 | Okamura et al. |
| 2013/0030569 A1 | 1/2013 | Fudaba et al. |
| 2013/0041292 A1 | 2/2013 | Cunningham |
| 2013/0274712 A1 | 10/2013 | Schecter |
| 2013/0282038 A1 | 10/2013 | Dannaher et al. |
| 2013/0282052 A1 | 10/2013 | Aranyi et al. |
| 2013/0324999 A1 | 12/2013 | Price et al. |
| 2013/0325029 A1 | 12/2013 | Hourtash et al. |
| 2013/0325030 A1 | 12/2013 | Hourtash et al. |
| 2014/0005667 A1* | 1/2014 | Stulen ............ A61B 17/320092 606/45 |
| 2014/0005718 A1 | 1/2014 | Shelton, IV et al. |
| 2014/0052150 A1* | 2/2014 | Taylor ................. A61F 9/00727 606/130 |
| 2014/0154039 A1 | 6/2014 | Downie et al. |
| 2014/0236177 A1 | 8/2014 | Verner et al. |
| 2014/0263539 A1 | 9/2014 | Leimbach et al. |
| 2014/0276931 A1 | 9/2014 | Parihar et al. |
| 2014/0276952 A1 | 9/2014 | Hourtash et al. |
| 2015/0018841 A1 | 1/2015 | Seo |
| 2015/0127151 A1 | 5/2015 | Riedel et al. |
| 2015/0209573 A1* | 7/2015 | Hibner ..................... A61N 1/00 606/48 |
| 2015/0234375 A1 | 8/2015 | Takayama |
| 2015/0282825 A1 | 10/2015 | Trees et al. |
| 2015/0313667 A1 | 11/2015 | Allen, IV |
| 2015/0342695 A1 | 12/2015 | He et al. |
| 2016/0199138 A1 | 7/2016 | Cooper et al. |
| 2016/0256184 A1 | 9/2016 | Shelton, IV et al. |
| 2016/0354169 A1 | 12/2016 | Suttin et al. |
| 2017/0246743 A1 | 8/2017 | Swarup et al. |
| 2017/0273748 A1* | 9/2017 | Hourtash ............... A61B 34/30 |
| 2017/0348854 A1 | 12/2017 | Oleynik |
| 2018/0049820 A1 | 2/2018 | Widenhouse et al. |
| 2018/0049821 A1 | 2/2018 | Shelton, IV et al. |
| 2018/0071050 A1 | 3/2018 | Nowatschin et al. |

OTHER PUBLICATIONS

U.S. Appl. No. 15/131,963 entitled "Method for Operating a Surgical Instrument" filed on Apr. 18, 2016.
U.S. Appl. No. 15/177,430 entitled "Surgical Instrument With User Adaptable Techniques" filed on Jun. 9, 2016.

* cited by examiner

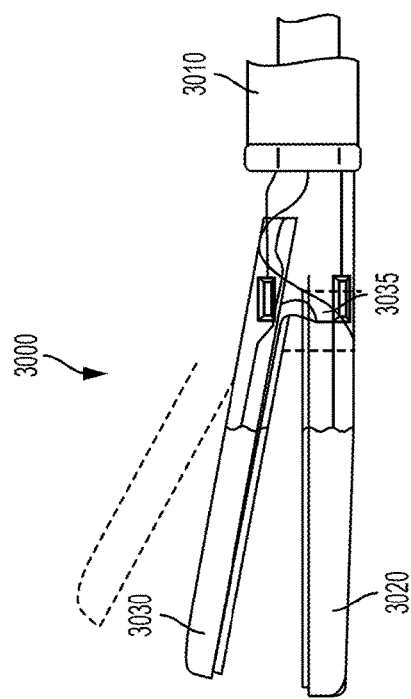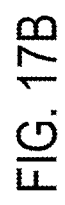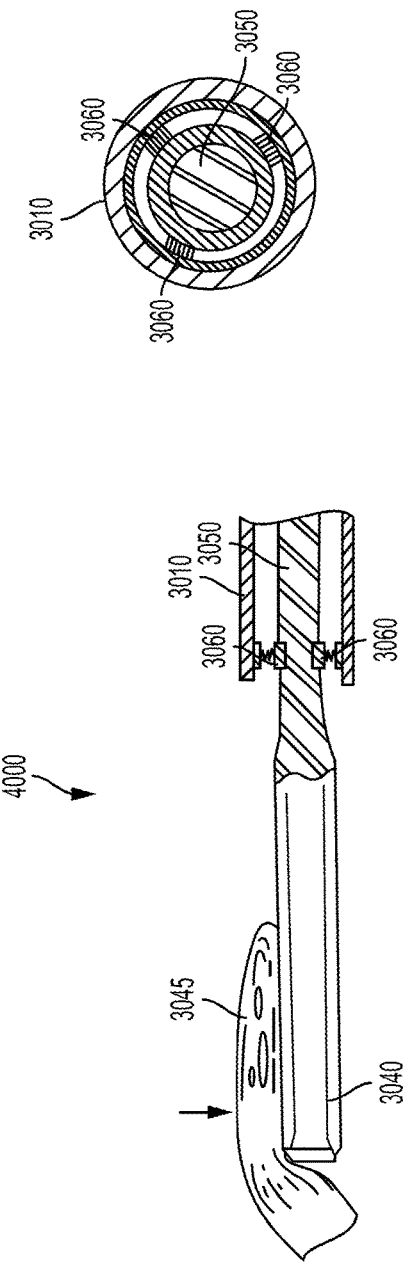

CONTROL OF ADVANCEMENT RATE AND APPLICATION FORCE BASED ON MEASURED FORCES

FIELD

Methods and devices are provided for robotic surgery, and in particular for sensing a force applied to a part of a surgical tool coupled to a robotic surgical system and controlling a movement parameter of at least one surgical arm of the robotic surgical system based on the sensed force.

BACKGROUND

Minimally invasive surgical (MIS) instruments are often preferred over traditional open surgical devices due to the reduced post-operative recovery time and minimal scarring. Laparoscopic surgery is one type of MIS procedure in which one or more small incisions are formed in the abdomen and a trocar is inserted through the incision to form a pathway that provides access to the abdominal cavity. The trocar is used to introduce various instruments and tools into the abdominal cavity, as well as to provide insufflation to elevate the abdominal wall above the organs. The instruments and tools can be used to engage and/or treat tissue in a number of ways to achieve a diagnostic or therapeutic effect. Endoscopic surgery is another type of MIS procedure in which elongate flexible shafts are introduced into the body through a natural orifice.

Although traditional minimally invasive surgical instruments and techniques have proven highly effective, newer systems may provide even further advantages. For example, traditional minimally invasive surgical instruments often deny the surgeon the flexibility of tool placement found in open surgery. Difficulty is experienced in approaching the surgical site with the instruments through the small incisions. Additionally, the added length of typical endoscopic instruments often reduces the surgeon's ability to feel forces exerted by tissues and organs on the end effector. Furthermore, coordination of the movement of the end effector of the instrument as viewed in the image on the television monitor with actual end effector movement is particularly difficult, since the movement as perceived in the image normally does not correspond intuitively with the actual end effector movement. Accordingly, lack of intuitive response to surgical instrument movement input is often experienced. Such a lack of intuitiveness, dexterity and sensitivity of endoscopic tools has been found to be an impediment in the increased the use of minimally invasive surgery.

Over the years a variety of minimally invasive robotic systems have been developed to increase surgical dexterity as well as to permit a surgeon to operate on a patient in an intuitive manner. Telesurgery is a general term for surgical operations using systems where the surgeon uses some form of remote control, e.g., a servomechanism, or the like, to manipulate surgical instrument movements, rather than directly holding and moving the tools by hand. In such a telesurgery system, the surgeon is typically provided with an image of the surgical site on a visual display at a location remote from the patient. The surgeon can typically perform the surgical procedure at the location remote from the patient whilst viewing the end effector movement on the visual display during the surgical procedure. While viewing typically a three-dimensional image of the surgical site on the visual display, the surgeon performs the surgical procedures on the patient by manipulating master control devices at the remote location, which master control devices control motion of the remotely controlled instruments.

While significant advances have been made in the field of robotic surgery, there remains a need for improved methods, systems, and devices for use in robotic surgery.

SUMMARY

Aspects of the current subject matter include a robotic surgical system having a control system that can monitor a variety of forces applied to the end effector, including a cutting tool associated with the end effector. In some implementations, the control system can control either an orientation or movement property (e.g., velocity) of at least one robotic arm, tool assembly, and/or end effector. Such control by the control system can be based on one or more of the monitored forces.

In one aspect, a robotic surgical system is described that includes a first robotic arm and a first tool assembly coupled to the first robotic arm. The first tool assembly can include a first shaft extending distally from a first housing and a first end effector coupled to a first distal end of the first shaft. The first end effector can be configured to manipulate a tissue of a patient. The first tool assembly can further include a first sensor operatively coupled to the end effector and configured to sense a first force applied to the first end effector by the tissue. The robotic surgical system can further include a second robotic arm and a second tool assembly coupled to the second robotic arm. The second tool assembly can include a second shaft extending distally from a second housing and a second end effector coupled to a second distal end of the second shaft. The second end effector can be configured to treat the tissue. Furthermore, the robotic surgical system can include a control system configured to control, based on the sensed first force applied to the end effector, a velocity of movement of the second end effector.

In some variations one or more of the following features can optionally be included in any feasible combination. The second end effector can include a cutting tool that is configured to cut the tissue. The second tool assembly can further include a second sensor that is configured to sense a second force applied to the second end effector in contact with tissue. The force applied to the second end effector by the tissue can be tissue tension and the control system can be further configured to control, based on at least one of the sensed tissue tension and the sensed second force applied to the second end effector, the velocity of movement of the second end effector relative to the tissue to thereby control the force applied to the second end effector. The control system can be further configured to control, based on the sensed first force, a positioning of the first arm to thereby increase or decrease the first force, where the first force can be tissue tension. The cutting tool can include a blade. The cutting tool can be configured to deliver one or more of an ultrasonic energy and a radio frequency energy to the tissue for assisting with cutting the tissue. The first end effector can include a pair of jaws that are configured to grasp the tissue. The robotic surgical system can further include a positioning device that controls an orientation between the first shaft and the second shaft. The positioning device can include a first support that releasably secures the first shaft and a second support that releasably secures the second shaft and at least one of the first support and the second support can be movable along a radial track of the positioning device. The first sensor and the second sensor can include a strain gauge. The movement of the second end effector can be effected by movement of at least one of the second robotic arm, the second tool assembly independent of the second robotic arm, and the second end effector independent of at least one of the second robotic arm and the second tool assembly.

In another interrelated aspect of the current subject matter, a method includes securing a part of a tissue of a patient to a first end effector of a first tool assembly coupled to a first robotic arm of a robotic surgical system. The method can further include sensing, with a first sensor operatively coupled to the first end effector, a tension in the tissue. In addition, the method can include controlling, based on the sensed tension, a velocity of movement of a second tool assembly coupled to a second robotic arm of the robotic surgical system. Additionally, the method can include sensing, with a second sensor operatively coupled to a second end effector of a second tool assembly coupled to the second robotic arm, a force applied to a cutting tool of the second end effector and controlling, based on the sensed force, the velocity of movement of the second tool assembly to thereby cause the sensed force to be within a desired force range. The method can further include controlling, based on the sensed tension in the tissue, a positioning of the first arm to thereby cause the tension in the tissue to be within a desired tension range. The velocity of movement can include a velocity at which the cutting tool cuts the tissue and the tissue can create the applied force against the cutting tool. The first sensor and second sensor can include a strain gauge.

The details of one or more variations of the subject matter described herein are set forth in the accompanying drawings and the description below. Other features and advantages of the subject matter described herein will be apparent from the description and drawings, and from the claims.

BRIEF DESCRIPTION OF THE DRAWINGS

The invention will be more fully understood from the following detailed description taken in conjunction with the accompanying drawings, in which:

FIG. 15A illustrates the distal end of the cutting tool of FIG. 14 positioned a distance from a tissue of a patient.

FIG. 16 illustrates another embodiment of end effector positioned at a distal end of a shaft of a tool assembly that is coupled to a robotic arm with the end effector including first and second jaws that are configured to releasably capture tissue therebetween.

FIG. 17A illustrates a section of tissue applying a force against a distal end of a blade that is positioned along a first jaw of the end effector with a proximal end of the blade being coupled to a strain gauge for measuring tension in the tissue.

FIG. 17B illustrates a cross sectional view of the shaft of FIG. 17A showing at least one strain gauge positioned adjacent the blade.

DETAILED DESCRIPTION

Figure 1:
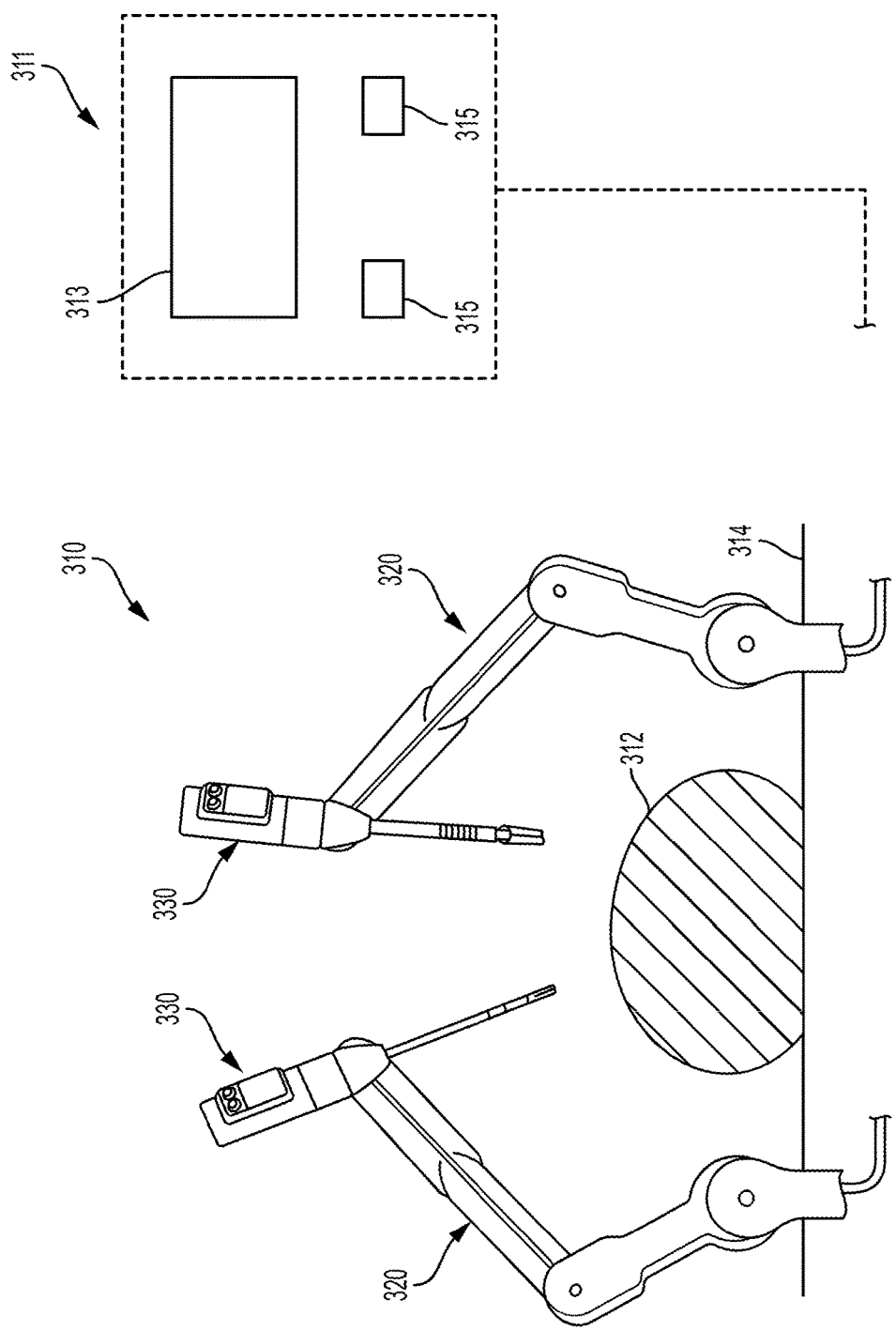
FIG. 1 illustrates a perspective view of an embodiment of a surgical robotic system that includes a patient-side portion and a user-side portion.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

In general, a surgical robotic system is described that can assist with performing surgical procedures on a patient. Such procedures can require the robotic surgical system to move a surgical arm and manipulate a tool assembly coupled to the robotic arm. For example, a tool assembly can include an end effector positioned at a distal end of a shaft. The end effector can include a blade or cutting tool that assists with making an incision or boring through tissue. The robotic surgical system can further include a control system that controls movement of the robotic arm for assisting with cutting or boring the tissue with the cutting tool. Movement of the robotic arm can be controlled either directly by the control system or by a user interacting with the control system. Typically, when a surgeon directly manipulates a cutting tool to cut through tissue, the surgeon can sense and rely upon tissue characteristics (e.g., tension, compression, etc.) and/or forces applied at a distal end of the cutting tool by the tissue being cut. Such characteristics and sensed forces can be used by the surgeon to determine a variety of aspects of the tissue relative to the cutting tool. For example, the surgeon can determine that the tissue does not have a desired amount of tension for advancing a cutting tool into the tissue to form an incision, thus the surgeon can increase tension in the tissue. In addition, the surgeon can sense a decrease in forces applied at the distal end of the cutting tool thereby indicating to the surgeon that the cutting tool is cutting through or has cut through the tissue. The ability to sense such forces, which is non-existent in robotic surgery, can allow the surgeon to determine how and when to move the cutting tool in order to perform the cutting of the tissue in a preferred way, as well as prevent from undesired cutting of tissue. As such, in order to perform efficient and effecting cutting of tissue, as well as cut tissue to a desired extent and prevent undesired cutting of tissue, the surgical robotic system described herein includes one or more sensors that sense a variety of forces associated with cutting of tissue with a part of the end effector (e.g., a boring or cutting tool). Such sensed forces are used by the control system to control either the end effector (e.g., jaw configuration, energy delivery, etc.) or at least one robotic arm (e.g., direction of movement and/or velocity of movement), as will be discussed in greater detail below.

As indicated above, in one embodiment the systems, devices, and methods disclosed herein can be implemented using a robotic surgical system. As will be appreciated by a person skilled in the art, electronic communication between various components of a robotic surgical system can be wired or wireless. A person skilled in the art will also appreciate that all electronic communication in the system can be wired, all electronic communication in the system can be wireless, or some portions of the system can be in wired communication and other portions of the system can be in wireless communication.

FIG. 1 is a perspective view of one embodiment of a surgical robotic system 300 that includes a patient-side portion 310 that is positioned adjacent to a patient 312, and a user-side portion 311 that is located a distance from the patient, either in the same room and/or in a remote location. The patient-side portion 310 generally includes one or more robotic arms 320 and one or more tool assemblies 330 that are configured to releasably couple to a robotic arm 320. The user-side portion 311 generally includes a vision system 313 for viewing the patient 312 and/or surgical site, and a control system 315 for controlling the movement of the robotic arms 320 and each tool assembly 330 during a surgical procedure.

The control system 315 can have a variety of configurations and it can be located adjacent to the patient, e.g., in the operating room, remote from the patient, e.g., in a separate control room, or it can be distributed at two or more locations. For example, a dedicated system control console can be located in the operating room, and a separate console can be located in a remote location. The control system 315 can include components that enable a user to view a surgical site of a patient 312 being operated on by the patient-side portion 310 and/or to control one or more parts of the patient-side portion 310 (e.g., to perform a surgical procedure at the surgical site 312). In some embodiments, the control system 315 can also include one or more manually-operated input devices, such as a joystick, exoskeletal glove, a powered and gravity-compensated manipulator, or the like. These input devices can control teleoperated motors which, in turn, control the movement of the surgical system, including the robotic arms 320 and tool assemblies 330.

The patient-side portion can also have a variety of configurations. As depicted in FIG. 1, the patient-side portion 310 can couple to an operating table 314. However, in some embodiments, the patient-side portion 310 can be mounted to a wall, to the ceiling, to the floor, or to other operating room equipment. Further, while the patient-side portion 310 is shown as including two robotic arms 320, more or fewer robotic arms 320 may be included. Furthermore, the patient-side portion 310 can include separate robotic arms 320 mounted in various positions, such as relative to the surgical table 314 (as shown in FIG. 1). Alternatively, the patient-side portion 310 can include a single assembly that includes one or more robotic arms 320 extending therefrom.

Figure 2:
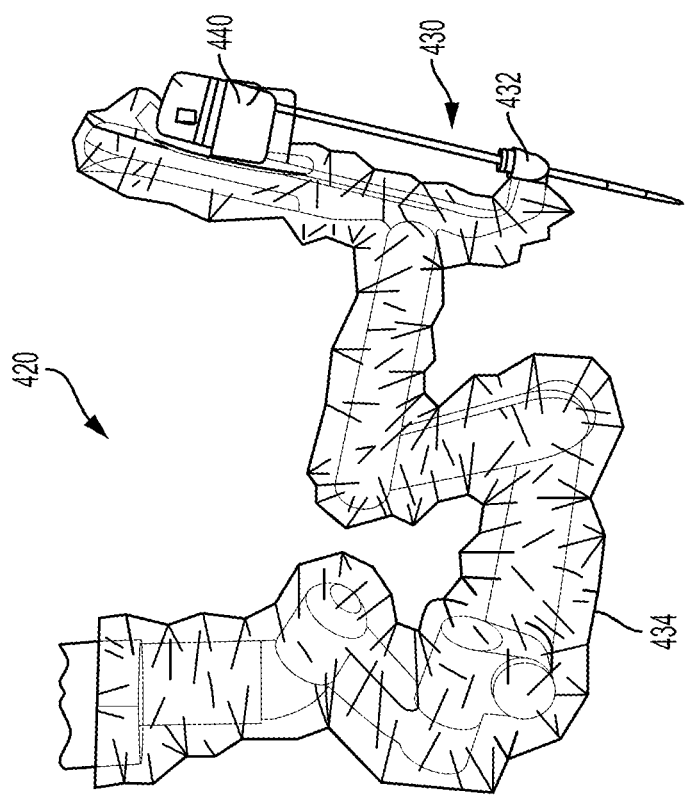
FIG. 2 illustrates an embodiment of a robotic arm of the surgical robotic system of FIG. 1 with a tool assembly releasably coupled to the robotic arm.

FIG. 2 illustrates one embodiment of a robotic arm 420 and a tool assembly 430 releasably coupled to the robotic arm 420. The robotic arm 420 can support and move the associated tool assembly 430 along one or more mechanical degrees of freedom (e.g., all six Cartesian degrees of freedom, five or fewer Cartesian degrees of freedom, etc.).

The robotic arm 420 can include a tool driver 440 at a distal end of the robotic arm 420, which can assist with controlling features associated with the tool assembly 430.

The robotic arm 420 can also include an entry guide 432 (e.g., a cannula mount or cannula) that can be a part of or removably coupled to the robotic arm 420, as shown in FIG. 2. A shaft 436 of the tool assembly 430 can be inserted through the entry guide 430 for insertion into a patient.

In order to provide a sterile operation area while using the surgical system, a barrier 434 can be placed between the actuating portion of the surgical system (e.g., the robotic arm 420) and the surgical instruments (e.g., the tool assembly 430). A sterile component, such as an instrument sterile adapter (ISA), can also be placed at the connecting interface between the tool assembly 430 and the robotic arm 420. The placement of an ISA between the tool assembly 430 and the robotic arm 420 can ensure a sterile coupling point for the tool assembly 430 and the robotic arm 420. This permits removal of tool assemblies 430 from the robotic arm 420 to exchange with other tool assemblies 430 during the course of a surgery without compromising the sterile surgical field.

Figure 3:
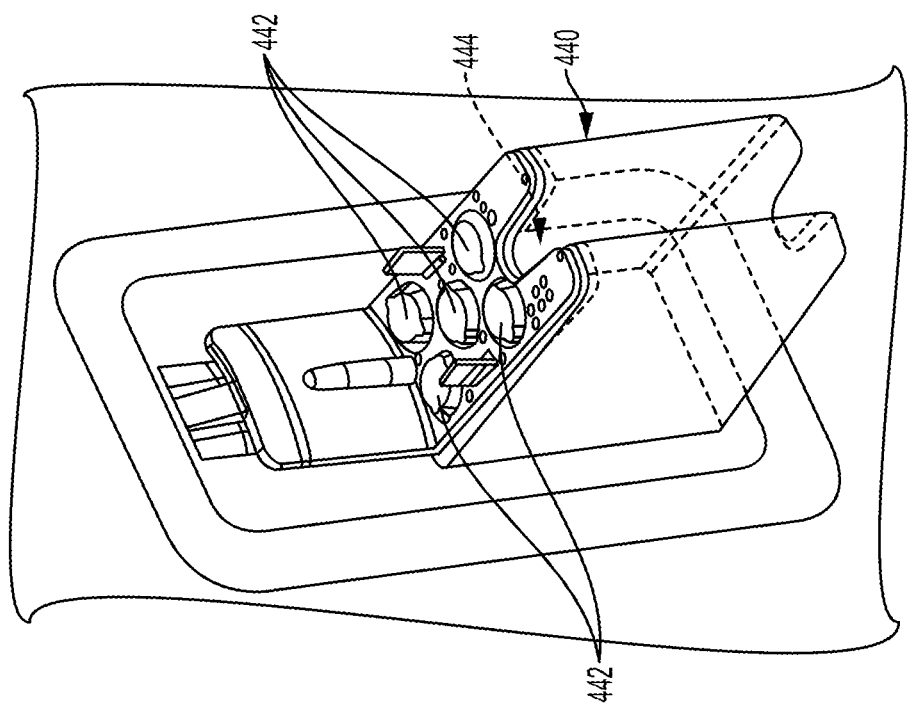
FIG. 3 illustrates an embodiment of a tool driver of the robotic arm of FIG. 2.

FIG. 3 illustrates the tool driver 440 in more detail. As shown, the tool driver 440 includes one or more motors, e.g., five motors 442 are shown, that control a variety of movements and actions associated with the tool assembly 430, as will be described in greater detail below. For example, each motor 442 can couple to and/or interact with an activation feature (e.g., gear) associated with the tool assembly 430 for controlling one or more actions and movements that can be performed by the tool assembly 430, such as for assisting with performing a surgical operation. The motors 442 are accessible on the upper surface of the tool driver 440, and thus the tool assembly is configured to mount on top of the tool driver 440 to couple thereto. The tool driver 440 also includes a shaft-receiving channel 444 formed in a sidewall thereof for receiving the shaft of the tool assembly 430. In other embodiments, the shaft can extend through on opening in the tool driver 440, or the two components can mate in various other configurations.

Figure 4:
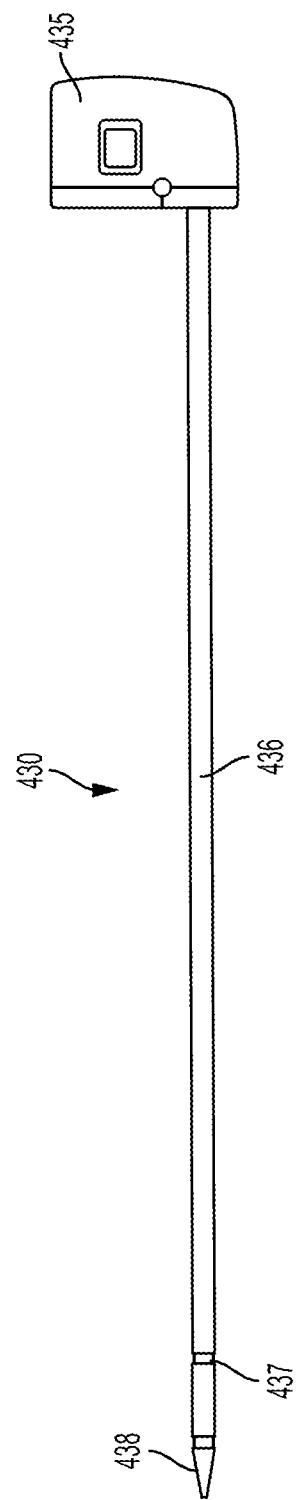
FIG. 4 illustrates the tool assembly of FIG. 2 uncoupled from the robotic arm, the tool assembly including a shaft extending from a puck at a proximal end and having an end effector located at a distal end of the shaft.

FIG. 4 illustrates the tool assembly 430 uncoupled from the robotic arm 420. The tool assembly 430 includes a housing or puck 435 coupled to a proximal end of a shaft 436 and an end effector 438 coupled to a distal end of the shaft 436. The end effector can include a pair of jaws, such as a second jaw that pivots relative to a first jaw. The second jaw can pivot between a closed position where the pair of jaws are configured to engage tissue therebetween and an open position where the pair of jaws are configured to receive tissue therebetween. A cartridge that holds staples can be disposed within the first jaw and one or more staples can be delivered to a surgical site upon firing of the end effector to staple tissue engaged therebetween. The puck 435 can include coupling features that assist with releasably coupling the puck 435 to the tool driver 440 of the robotic arm 420. The puck 435 can include gears and/or actuators that can be actuated by the one or more motors 442 in the driver 440, as will be described in greater detail below. The gears and/or actuators in the puck 435 can control the operation of various features associated with the end effector 438 (e.g., clamping, firing, rotation, articulation, energy delivery, etc.), as well as control the movement of the shaft 436 (e.g., rotation of the shaft).

The shaft 436 can be fixed to the puck 435, or it can be releasably coupled to the puck 435 such that the shaft 436 can be interchangeable with other shafts. This can allow a single puck 435 to be adaptable to various shafts 436 having different end effectors 438. The shaft 436 can include actuators and connectors that extend along the shaft and assist with controlling the actuation and/or movement of the end effector 438 and/or shaft 436. The shaft 436 can also include one or more joints or wrists 437 that allow a part of the shaft 436 or the end effector 438 to articulate relative to the longitudinal axis of the shaft 436. This can allow for fine movements and various angulation of the end effector 438 relative to the longitudinal axis of the shaft 436. The end effector 438 can include any of a variety of surgical tools, such as a stapler, a clip applies, forceps, a needle driver, a cautery device, a cutting tool, a pair of jaws, an imaging device (e.g., an endoscope or ultrasound probe), or a combined device that includes a combination of two or more various tools.

Figure 5:
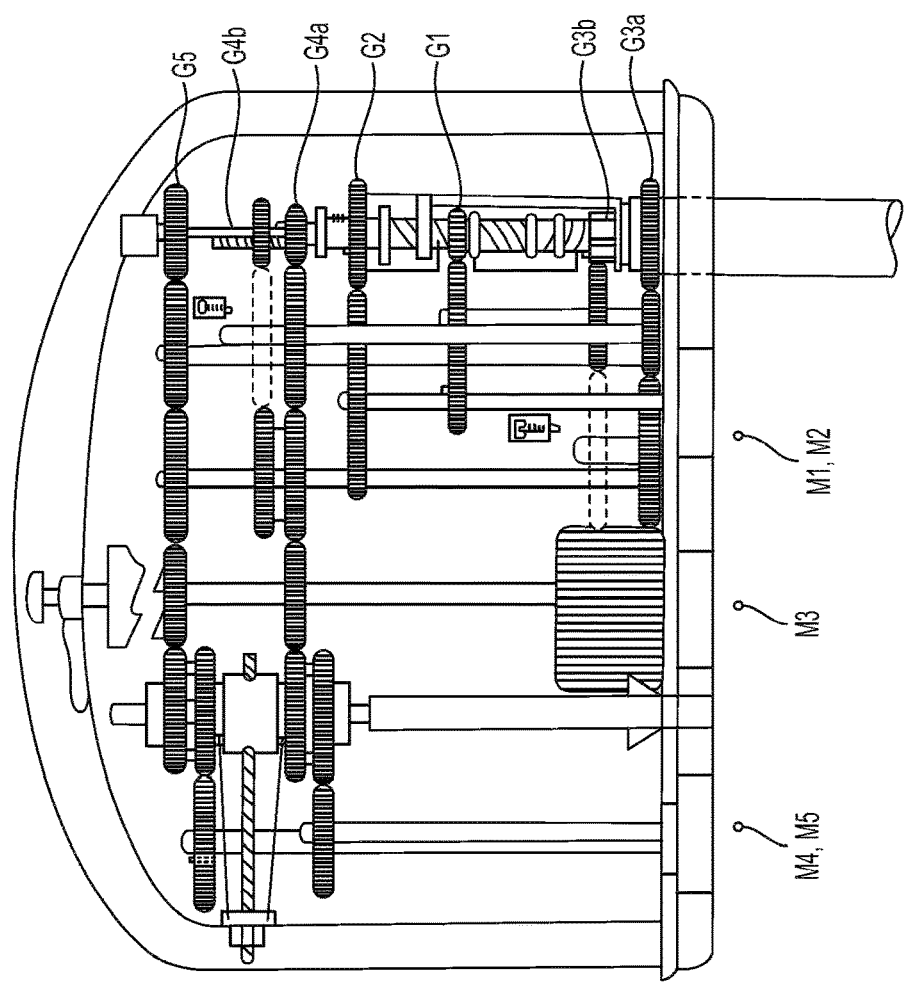
FIG. 5 illustrates an embodiment of puck of the tool assembly of FIG. 4.

FIG. 5 illustrates the puck 435 and a proximal end of a shaft 436 extending from the puck 435 in more detail. As shown in FIG. 5, the puck 435 includes a plurality of actuation gears and gear shafts that can be either directly or indirectly controlled to any one of the motors 442 associated with the driver 440. For example, as shown in FIG. 5, the puck 435 is configured to couple to five motors at the locations indicated by reference numbers M1, M2, M3, M4, and M5. In this embodiment, puck 435 includes first and second articulation gears G1, G2 that are coupled respectively to the first and second motors M1, M2 via a series of one or more additional gears and shafts. Actuation of the first and second motors M1, M2 will rotate the articulation gears G1, G2, which in turn cause linear movement of an articulation cable in a proximal or distal direction to thereby cause articulation of the end effector 438 in desired left and right directions. The puck 435 also includes a shaft rotation gear G3a that is coupled to the third motor M3 via a series of one or more additional gears and shafts. Actuation of the third motor M3 will thus rotate the shaft rotation gear G3a thereby causing rotation of the shaft 436 of the tool assembly 430. The third motor M3 can also be configured to shift and to couple, via a series of one or more additional gears and shafts, to a head rotation gear G3b which will cause rotation of the end effector 438 relative to the shaft 436. The puck 435 further includes a firm close gear G4a that is coupled to the fourth motor M4 via a series of one or more additional gears and shafts. Actuation of the fourth motor M4 will rotate the firm close gear G4a to cause linear translation of a drive screw to firmly close the jaws of the end effector 438. The puck 435 further includes a quick close gear G4b that can also couple to the fourth motor M4 via a series of one or more additional gears and shafts. When motor M4 is shifted into engagement with the quick close gear G4b, actuation of the fourth motor M4 will rotate the quick close gear G4b to cause linear translation of a quick close cable to quickly close the jaws of the end effector 438. Finally, the illustrated puck 435 includes a firing gear G5 that is coupled to the fifth motor M5 via a series of one or more additional gears and shafts. Actuation of the fifth motor M5 will rotate the firing gear G5, thereby driving a lead screw linearly to advance a sled through the end effector 438, as will be discussed in more detail below.

Figure 6:
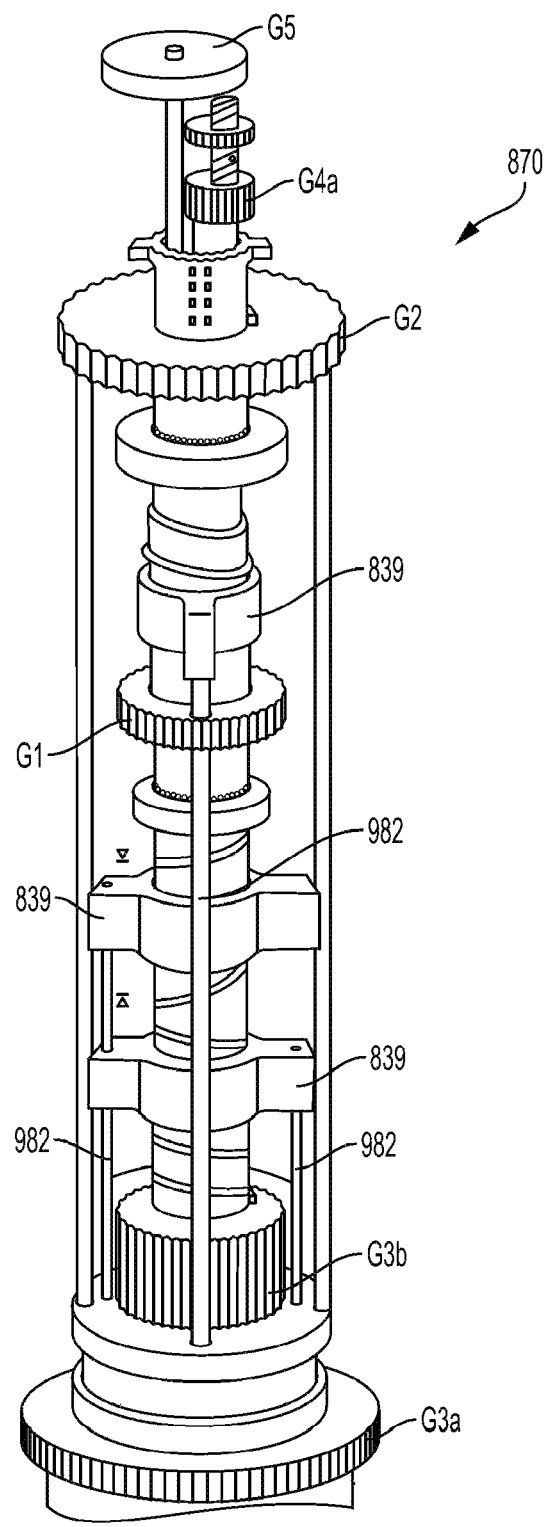
FIG. 6 illustrates an embodiment of an actuation assembly of the puck of FIG. 5.
Figure 7:
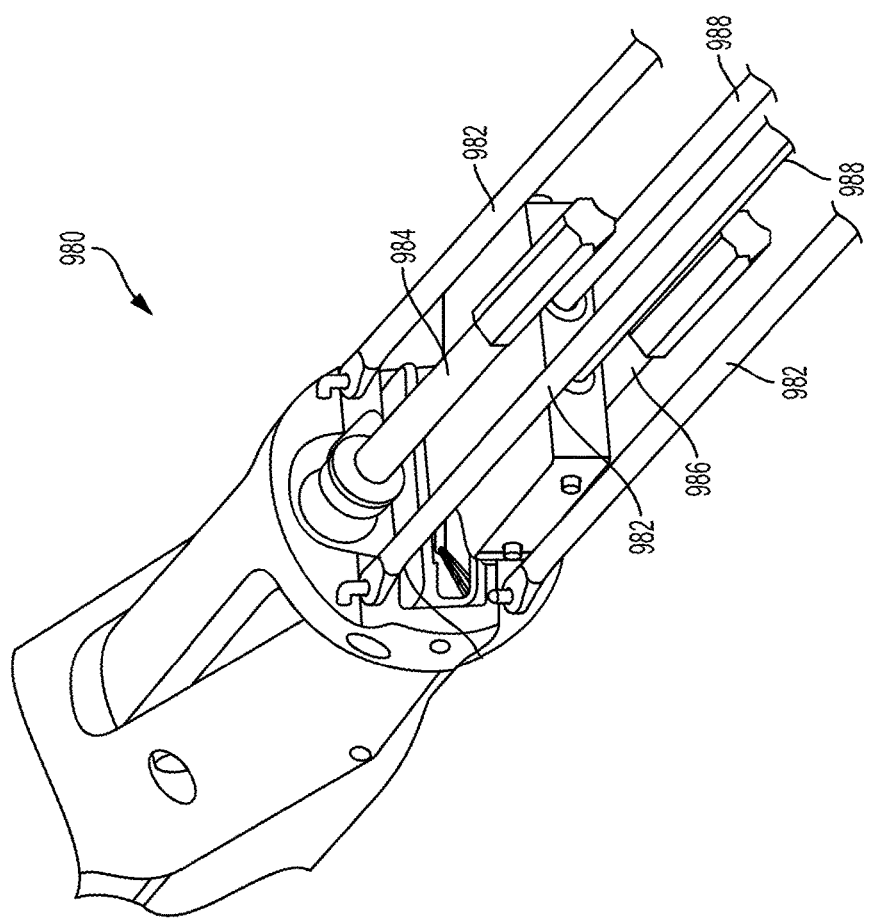
FIG. 7 illustrates an embodiment of actuation shafts extending from a wrist located just proximal of the end effector of FIG. 4.

FIG. 6 illustrates the actuation assembly 870 components of the puck 435 of FIG. 5. As shown and indicated above, each of the gears G1-G5 is coupled to an actuation shaft that extends from the actuation assembly 870 and along the shaft 436 of the tool assembly 430, such as for controlling the movements of the end effector. FIG. 7 illustrates a distal end of the actuation shafts extending from a wrist 980 located just proximal of the end effector 438. The wrist 980 can allow for fine movements and angulation of the end effector 438 relative to the proximal end of the shaft 436. As shown in FIG. 7, the wrist 980 includes four articulation cables 982 that are spaced around a perimeter of the wrist 980. When actuated (e.g., pushed, pulled, rotated), the articulation cables 982 will cause articulation of the end effector 438 (e.g., movement up, down, left, right, and combinations thereof) relative to the proximal end of the shaft 436. The articulation cables 982 are connected to the articulation couplers 839, shown in FIG. 6, that are driven proximally and distally when the articulation gears G1, G2 are actuated by the first and second motors M1, M2. The wrist 980 also includes an upper rotary driver 984 that when actuated can cause the pair of jaws of the end effector 438 to firmly close. The upper rotary driver 984 is coupled to the firm close gear G4a shown in FIG. 6 such that rotation of the firm close gear G4a by the motor M4 causes rotation of the rotary driver 984. The wrist 980 can also include a lower rotary driver 986 that when actuated can cause movement of a sled located at the end effector 438. The lower rotary driver 986 is coupled to the firing gear G5 shown in FIG. 6 and it likewise rotates in response to rotation of the firing gear G5. The illustrated wrist 980 further includes a linear pull cable 988 that is coupled to the quick close gear G4b shown in FIG. 6 and that moves linearly in a proximal direction to cause rapid close of the pair of jaws.

Figure 8:
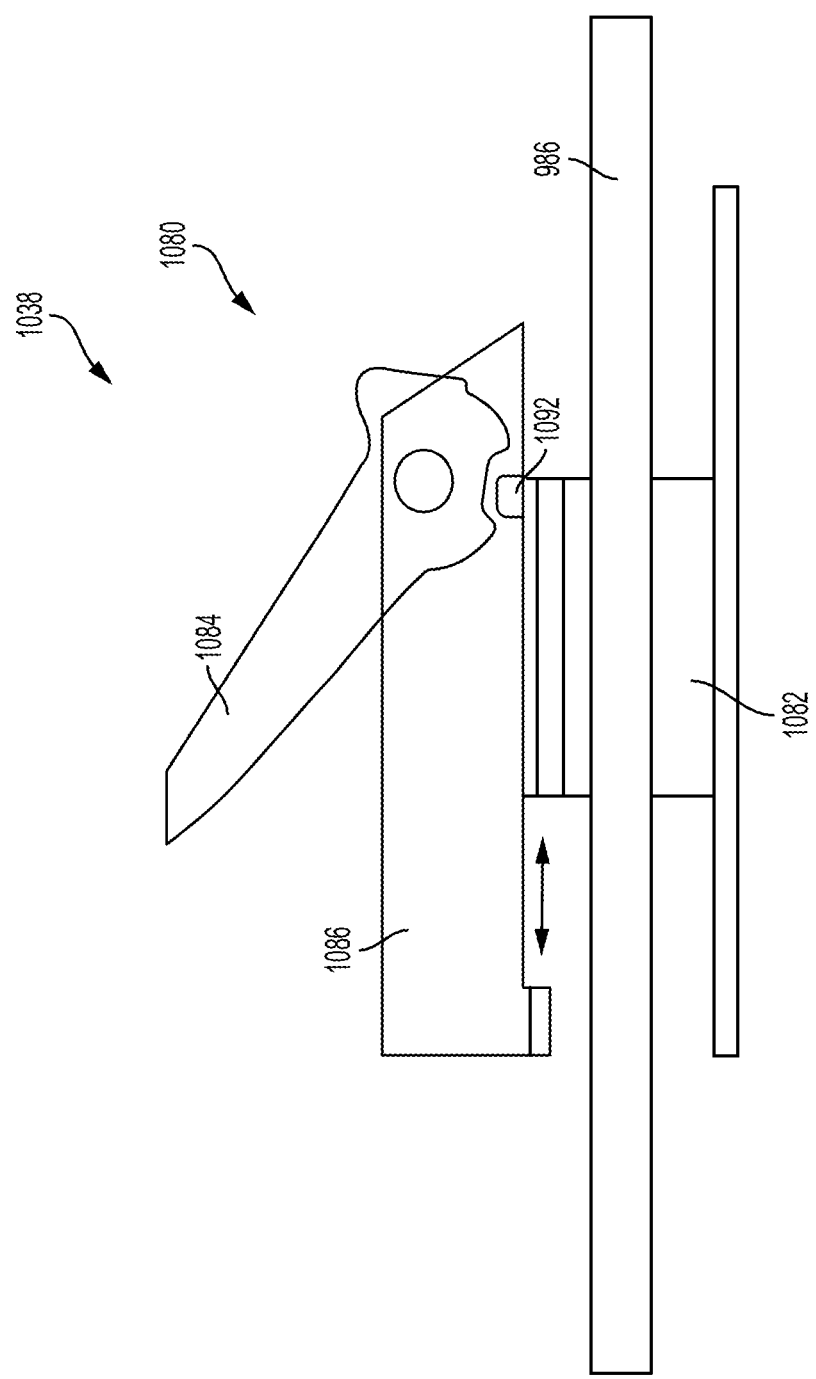
FIG. 8 illustrates a portion of the end effector of FIG. 7.

FIG. 8 illustrates a portion of an end effector 1038 having a knife actuation assembly 1080 that includes a drive member 1082, a knife 1084, a knife sled 1086, and a lead screw or rotary driver 986. The drive member 1082 includes internal threads that are threadably coupled with the rotary driver 986. Such coupling can allow drive member 1082 to move along the rotary driver 986 when the rotary driver 986 is rotated. As discussed above, the rotary driver 986 can be actuated at the wrist 980, as shown in FIG. 7, thereby causing rotation of the rotary driver 986 and linear movement of the knife sled 1086 along the rotary driver 986. The rotary driver 986 is coupled to the firing gear G5 shown in FIG. 6. The knife actuation assembly 1080 is configured to orient the knife 1084 in a cutting position when the drive member 1082 pushes the knife sled 1086 along the rotary driver 986 and to stow the knife 1084 when the drive member 1082 is moved proximally relative to the knife sled 1086. In operation, the rotary driver 986 is first rotated to advance the drive member 1082 distally along the rotary driver 986 thereby pushing the knife sled 1086 in the distal direction and angularly orienting the knife 1084 in the cutting position. At the end of the distal movement of the assembly 1080, the direction of rotation of the rotary driver 986 is reversed to retract the drive member 1082 proximally relative to the knife sled 1086, thereby causing the knife 1084 to rotate down into the stowed position, such as via interaction between an interface feature 1092 and the knife 1084.

Figure 9:
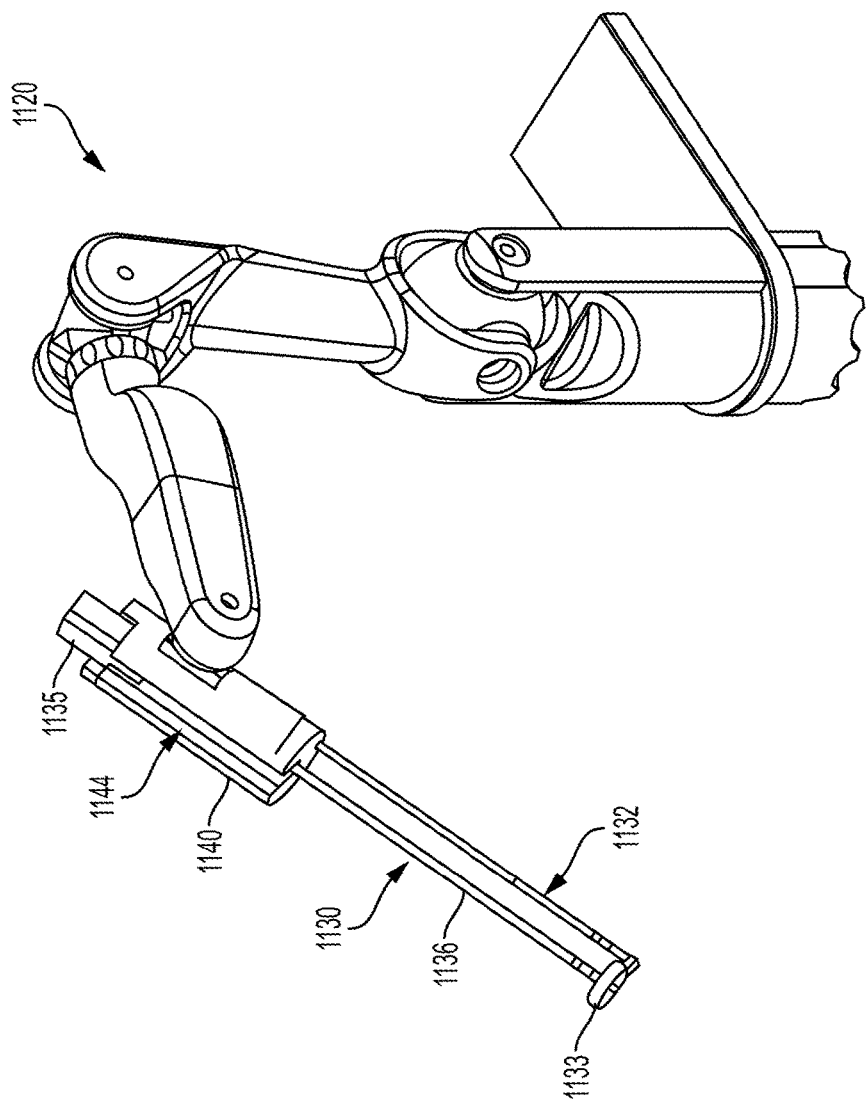
FIG. 9 illustrates another embodiment of a robotic arm and another embodiment of a tool assembly releasably coupled to the robotic arm.

FIG. 9 illustrates another embodiment of a robotic arm 1120 and a tool assembly 1130 releasably coupled to the robotic arm 1120. The robotic arm 1120 can support and move the associated tool assembly 1130 along one or more mechanical degrees of freedom (e.g., all six Cartesian degrees of freedom, five or fewer Cartesian degrees of freedom, etc.).

The robotic arm 1120 can include a tool driver 1140 at a distal end of the robotic arm 1120, which can assist with controlling features associated with the tool assembly 1130. The robotic arm 1120 can also include a movable tool guide 1132 that can retract and extend relative to the driver 1140. A shaft of the tool assembly 1130 can extend parallel to a threaded shaft of the movable tool guide 1132 and can extend through a distal end feature 1133 (e.g., a ring) of the movable tool guide 1130 and into a patient.

In order to provide a sterile operation area while using the surgical system, a barrier (not shown) can be placed between the actuating portion of the surgical system (e.g., the robotic arm 1120) and the surgical instruments (e.g., the tool assembly 1130) in the sterile surgical field. A sterile component, such as an instrument sterile adapter (ISA), can also be placed at the connecting interface between the tool assembly 1130 and the robotic arm 1120. The placement of an ISA between the tool assembly 1130 and the robotic arm 1120 can ensure a sterile coupling point for the tool assembly 1130 and the robotic arm 1120. This permits removal of tool assemblies 1130 from the robotic arm 1120 to exchange with other tool assemblies 1130 during the course of a surgery without compromising the sterile surgical field.

Figure 10:
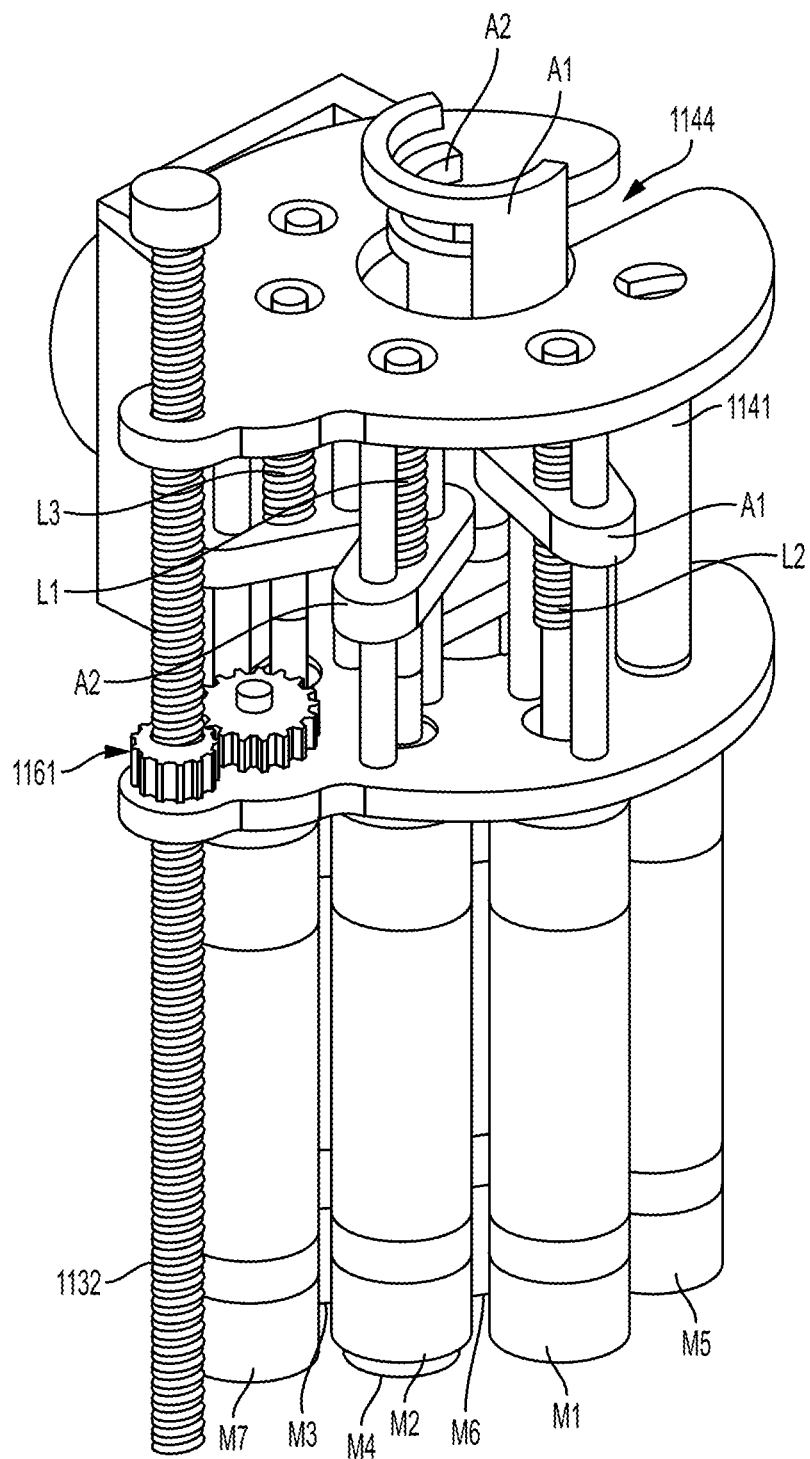
FIG. 10 illustrates a tool driver of the robotic arm of FIG. 9 having one or more motors that control a variety of movements and actions associated with the tool assembly.

FIG. 10 illustrates the tool driver 1140 in more detail. As shown, the tool driver 1140 includes one or more motors, e.g., seven motors M1-M7 are shown, that control a variety of movements and actions associated with the tool assembly 1130, as will be described in greater detail below. The driver 1140 can also include one or more lead screws (e.g., three lead screws L1, L2, and L3 are shown) that can be individually rotated by a motor and, as a result of the rotation of the lead screw, cause linear and/or rotational movement of at least one actuator (e.g., see, for example, actuators A1 and A2 shown in FIG. 10). Movement of each actuator controls the movement of driving members (e.g., gears, cables) located in the tool assembly 1130 for controlling one or more actions and movements that can be performed by the tooling assembly 1130, such as for assisting with performing a surgical operation. The actuators extend from a top end of the driver 1140 for coupling to the driving members of the tool assembly 1130 mounted on top of the tool driver 1140.

The tool assembly 1130 can be loaded from a top side of the driver 1140 with the shaft of the tool assembly 1130 being positioned in a shaft-receiving channel 1144 formed along the side of the driver 1140. The shaft-receiving channel 1144 allows the shaft, which extends along a central axis of the tool assembly 1130, to extend along a central axis of the driver 1140 when the tool assembly 1130 is coupled to the driver 1140. In other embodiments, the shaft can extend through on opening in the tool driver 1140, or the two components can mate in various other configurations.

Figure 11:
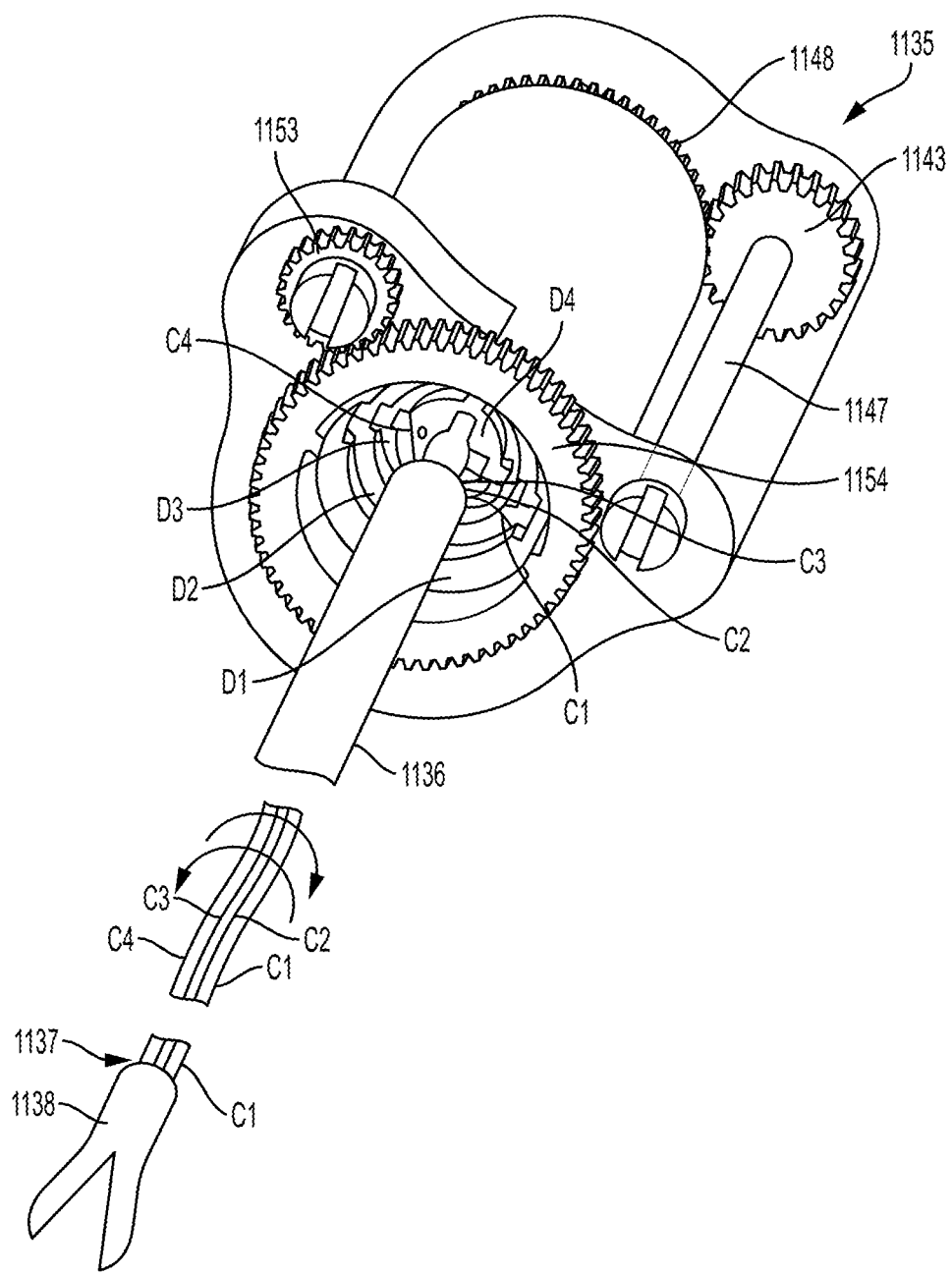
FIG. 11 illustrates a part of a puck actuation assembly contained within the puck of the tool assembly of FIG. 9.

As shown in FIGS. 9 and 11, the tool assembly 1130 includes a housing or puck 1135 coupled to a proximal end of a shaft 1136 and an end effector 1138 coupled to a distal end of the shaft 1136. The puck 1135 can include coupling features that assist with releasably coupling the puck 1135 to the tool driver 1140 of the robotic arm 1120. The puck 1135 can include driving members (e.g., gears, cables, and/or drivers) that can be directly or indirectly actuated by the one or more motors M1-M5, as will be described in greater detail below. The driving members in the puck 1135 can control the operation of various features associated with the end effector 1138 (e.g., clamping, firing, rotation, articulation, etc.), as well as control the movement of the shaft 1136 (e.g., rotation and/or articulation of the shaft).

The shaft 1136 can be releasably coupled to the puck 1135 such that the shaft 1136 can be interchangeable with other shafts. This can allow a single puck 1135 to be adaptable to various shafts 1136 having different end effectors 1138. The shaft 1136 can include actuators and connectors that extend along the shaft and assist with controlling the actuation and/or movement of the end effector 1138 and/or shaft 1136. The shaft 1136 can also include one or more joints or wrists 1137 that allow a part of the shaft 1136 or the end effector 1138 to rotate and/or articulate relative to the longitudinal axis of the shaft 1136. This can allow for fine movements and various angulation of the end effector 1138 relative to the longitudinal axis of the shaft 1136. The end effector 1138 can include any of a variety of surgical tools, such as a stapler, a clip applier, forceps, a needle driver, a cautery device, a cutting tool, a pair of jaws, an imaging device (e.g., an endoscope or ultrasound probe), or a combined device that includes a combination of two or more various tools.

FIG. 11 illustrates a part of a puck actuation assembly contained within the puck 1135. As shown in FIG. 11, the puck 1135 includes at least one driving member (e.g., four driving members D1, D2, D3, and D4 are shown) that can each become engaged with an actuator of the driver 1140 such that actuation of an actuator causes actuation of a driving member thereby controlling the operation of various features associated with the shaft 1136 and/or end effector 1138. Each driving member D1-D4 can be coupled to a proximal end of a shaft or cable (e.g., four cables C1, C2, C3, and C4 are shown). Each cable can extend from a driving member and couple to a feature associated with either the shaft 1136 or the end effector 1138 thereby controlling a function of such feature.

Figure 12:
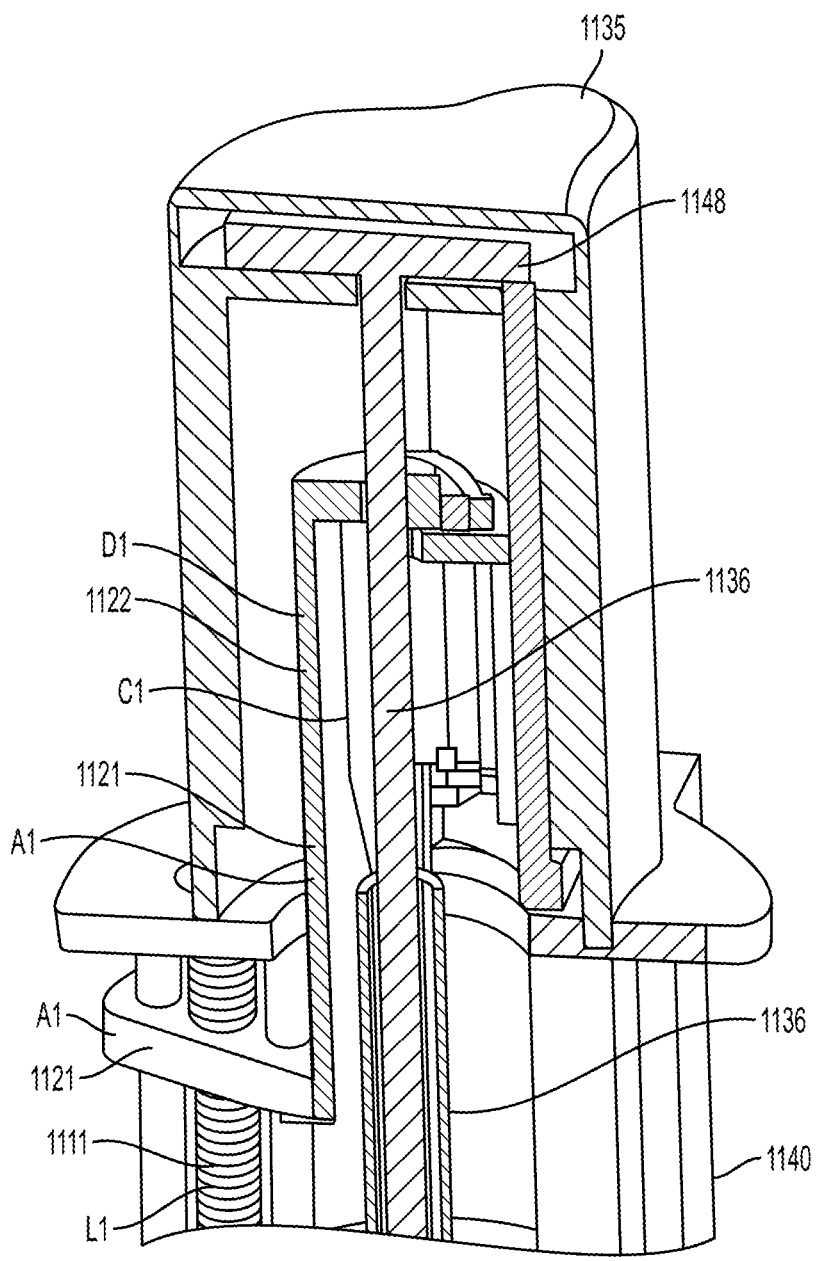
FIG. 12 illustrates the puck of FIG. 11 coupled to the driver with the actuators extending from the driver into the puck and engaging driving members.

FIG. 12 illustrates the puck 1135 coupled to the driver 1140 with the actuators extending from the driver 1140 into the puck 1135 and engaging the driving members. For example, motor M1 can cause lead screw L1 to rotate thereby causing actuator A1, which is threadably coupled to lead screw L1, to linearly advance in the proximal direction (towards and into the puck 1135). Actuator A1 can include an extension threadably coupled to the lead screw L1. The extension can be coupled to or integrated with a partial cylindrical shaft that extends along the longitudinal axis of the puck 1135 and the driver 1140. The partial cylindrical shaft of the actuator A1 can engage with driving member D1 such that when the actuator A1 is linearly advanced, the driving member D1 is caused to linearly advance in the same direction. Driving member D1 can be coupled to cable C1 such that when driving member D1 is advanced in the proximal direction, cable C1 is pulled in the proximal direction. Cable C1 extends along the shaft of the tool assembly 1130 and is operatively coupled to a part of the end effector 1138 thereby controlling a function of the end effector 1138 (e.g., opening and closing of jaws, deployment of a staple, etc.) when the cable is C1 translated in either the proximal or distal direction.

In some implementations, for example, four motors (e.g., M1-M4) can each individually control movement of a respective lead screw (e.g., L1-L4) thereby individually linearly translating a respective actuator (e.g., A1-A4) coupled thereto. Although the actuators are described as being linearly translated, the actuators can be linearly translated and/or rotationally moved as a result of actuation of a respective motor. Additional motors (e.g., motors M5 and M6) can be included in the driver 1140 for actuating various other aspects of the tool assembly 1130. For example, motor M5 can cause a first driver shaft 1141 to rotate, which is operatively coupled to a first puck shaft 1147 having a first puck gear 1143 coupled to a distal end of the first puck shaft 1147. Rotation of the first driver shaft 1141 thereby causes the first puck shaft 1147 and first puck gear 1143 to rotate. The first puck gear 1143 is engaged with a first shaft rotation gear 1148 that is caused to rotate as a result of the first puck gear 1143 rotating. The first shaft rotation gear 1148 is operatively coupled to the shaft 1136 of the tool assembly 1130 and can thereby cause rotation of the shaft 1136 and/or end effector 1138. Motor 146 can cause a second driver shaft to rotate, which is operatively coupled to a second puck gear 1153. The second puck gear 1153 is engaged with a second shaft rotation gear 1154 that is caused to rotate as a result of the second puck gear 1153 rotating. The second shaft rotation gear 1154 is also operatively coupled to the shaft 1136 and, upon rotation, provides additional torque through the shaft 1136 and for various features associated with the end effector 1138. Actuation of motor M7 can cause shaft gears 1161 to rotate, thereby causing the threaded shaft of the movable tool guide 1132 to linearly translate.

As discussed above, the robotic surgical system can include one or more robotic arms with each robotic arm having a tool assembly coupled thereto. Each tool assembly can include an end effector that has one or more of a variety of features, such as one or more tools for assisting with performing a surgical procedure. For example, the end effector can include a cutting or boring tool that can be used to perforate or cut through tissue (e.g., create an incision). Furthermore, some end effectors include one or more sensors that can sense a variety of characteristics associated with either the end effector or the tissue. Each robotic arm and end effector can be controlled by a control system to assist with creating a desired cut or bore and prevent against undesired cutting of tissue. As an alternative to (or in addition to) controlling the robotic arm, it is understood that the control system can control either the tool itself or the tool assembly.

One or more aspects associated with the movement of the robotic arm can be controlled by the control system, such as either a direction or a velocity of movement. For example, when boring through tissue, the robotic arm can be controlled to perform jackhammer-like movements with the cutting tool. Such jackhammer movements can include the robotic arm moving up and down along an axis (e.g., an axis that is approximately perpendicular to the tissue being perforated) in a rapid motion while also advancing the cutting tool in a downward direction towards the tissue to eventually perforate the tissue with the cutting tool (e.g. an ultrasonic blade). While performing such movements in a robotic surgical procedure, not only can it be difficult to see the tissue being perforated to thereby determine a relative position of the cutting tool, but it can also be difficult to determine when the cutting tool has completed perforating the tissue. Such position of the cutting tool relative to the tissue can include the cutting tool approaching or not yet in contact with the tissue, the cutting tool drilling down or cutting into the tissue, and the cutting tool extending through or having perforated the tissue. These positions can be difficult for either a user controlling the robotic arm or the robotic surgical system to determine which can result in potential harm to the patient due to over or under-penetrating the tissue, as well as result in longer procedure times. As such, in order to reduce procedure time and surgical errors, the robotic surgical system includes a control system that communicates with at least one sensor assembly configured to sense a force applied at a distal end of the end effector or cutting tool. The control system can thereby determine and control, based on such sensed forces, one or more appropriate aspects associated with the movement of the robotic arm, such as when boring or cutting into tissue, as will be described in greater detail below.

Although a cutting tool for perforating tissue is described in detail herein, the sensor assembly of the present disclosure that is in communication with the control system can be implemented in any number of robotic surgical systems for detecting any number of a variety of tools and/or end effectors used for performing any number of a variety of procedures without departing from the scope of this disclosure. Furthermore, any number of movements can be performed by the robotic arm to perforate or cut tissue using the robotic surgical system including the sensor assembly and control system described herein and is not limited to the jackhammering or boring of tissue.

Figure 13:
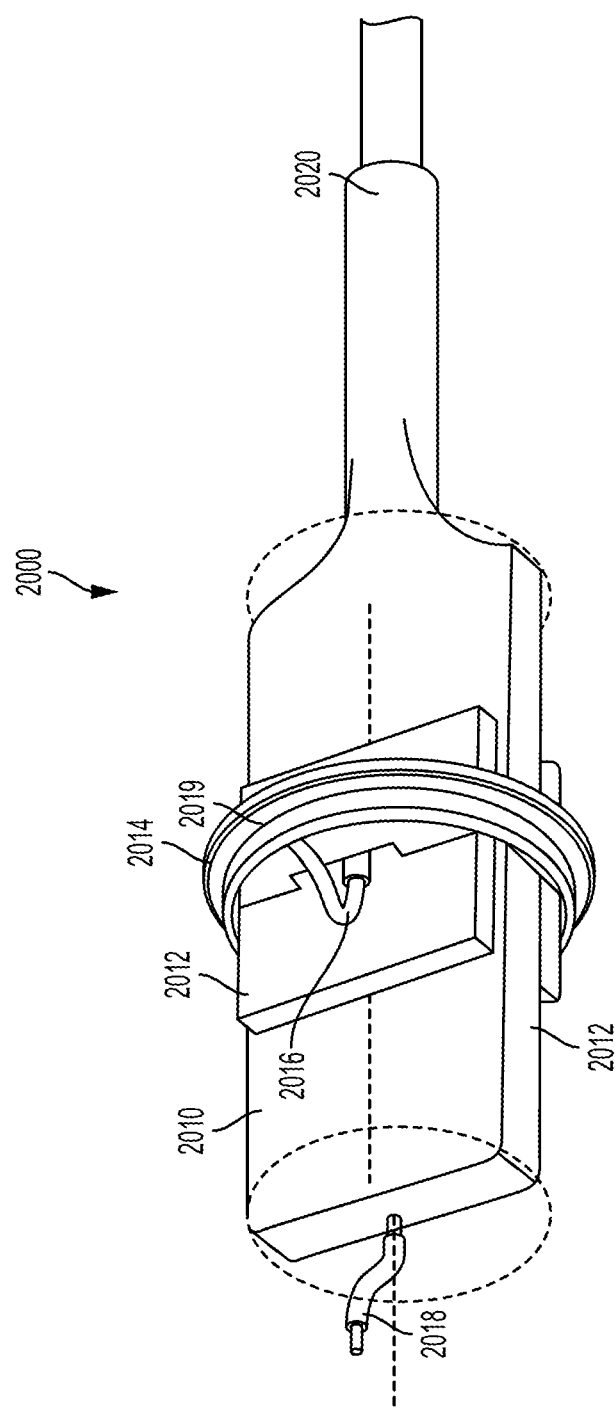
FIG. 13 illustrates an embodiment of a sensor assembly that is configured to sense an applied force along a part of the end effector of a tool assembly, such as the tool assemblies shown in FIGS. 4 and 9.

FIG. 13 illustrates an embodiment of a sensor assembly 2000 that is configured to sense a force applied along a part of the end effector of a tool assembly, such as the tool assemblies shown in FIGS. 4 and 9. The sensor assembly 2000 can be either positioned within or adjacent the end effector to sense such applied forces. The forces applied to the end effector can be along one or more of a variety of parts of the end effector, such as at a distal end, including a distal end of a tool (e.g., cutting tool) of the end effector. Such forces applied to the end effector can be sensed by the sensor assembly 2000, which can be collected and monitored by a control system of the robotic surgical system, such as the control system 315 in FIG. 1. The control system can use such sensed forces to determine and control movements associated with the robotic arm, such as to assist with cutting or boring through tissue.

The sensor assembly 2000 includes at least one blade 2010 that can be made out of a metallic material, such as titanium. The blade 2010 can be flat such that its width is significantly greater than its thickness. The sensor assembly 2000 can further include at least one plate 2012 that is made out of lead zirconate titanate (PZT). For example, a plate 2012 can be coupled to each side of the blade 2010, as shown in FIG. 13. As illustrated, the sensor assembly 2000 also includes a contact ring 2014 that encircles a part of either the blade 2010 or plate 2012. A first connecting wire 2016 extends between the plate 2012 and the contact ring 2014 and a ground 2018 extends from the blade 2010. In use, a voltage is applied to the contact ring 2014 and a strain gauge 2019 is coupled to the contact ring 2014, which can assist with measuring the applied force on the end effector. The sensor assembly 2000 can include one or more of a strain gauge and a piezo stack that sense a resistance load, which the control system can monitor for determining and controlling an appropriate velocity and/or direction of movement of the robotic arm.

In some embodiments, the strain gauge 2019 may be either adhered directly to the blade 2012 or end effector (e.g., one or both jaws) such that if the blade 2012 or end effector deflects or bends, the strain gauge 2019 will also bend. Applying loads to the end effector can result in biasing the blade 2019 and/or end effector perpendicular to the axis of the shaft. This movement can result in a load applied to the strain gauge 2019 mounted on the spring member. Alternatively or in addition, the strain gauge 2019 can be adhered to a spring member that is coupled to the shaft of the tool assembly. Deflection of the spring member as a result of deflection of the shaft can deflect the gauge 2019.

The tool assembly can include any number of configurations of sensors and circuits for measuring tissue parameters (e.g., temperature, tension, etc.) and/or tool assembly parameters (e.g., velocity, rotational speed, etc.). Such parameters can be used to determine appropriate tissue treatment and execution of the tool assembly. For example, any of the sensors described and/or contemplated herein, including the strain gauge 2019, can be a part of a flexible circuit. Such flexible circuits are described in co-pending and commonly owned patent application Ser. No. 15/177,430 that was filed Jun. 9, 2016 and entitled "SURGICAL INSTRUMENT WITH USER ADAPTABLE TECHNIQUES," of which the entire contents of this application is incorporated herein by reference. The flexible circuit can be coupled to and/or integrated into any part of the tool assembly, including the end effector, and can be in communication with the control system, such as the control system 315 in FIG. 1. For example, the control system 315 can collect data from the flexible circuit (e.g., sensed data by the sensor of the flexible circuit) to determine appropriate treatment and execution of the tool assembly.

In the exemplary embodiment, the sensor assembly 2000, which can include or be a part of a flexible circuit, is coupled to a part of the shaft adjacent the end effector to allow the sensor assembly 2000 to detect forces applied to the end effector, such as a distal end or cutting end of a cutting tool. As such, when a load that is perpendicular to the axis of the shaft is placed on the blade 2012 or end effector, the blade 2012 or end effector can deflect thereby causing the strain gauge 2019 to deflect. When deflected, the internal resistance of the strain gauge 2019 changes, thereby producing a strain reading that can be sent to the control system for analysis (e.g., measuring of strain, determining and control appropriate velocities and/or directions of movement of the robotic arm, etc.).

As shown in FIG. 13, the sensor assembly 2000 includes a waveguide 2020 that is configured to deliver energy to the tissue for assisting with cutting or boring through the tissue. For example, such energy can include ultrasonic energy or radio frequency energy. The waveguide 2020 can be in communication with the sensor assembly 2000 such that the sensor assembly 2000 can sense a pressure or force applied to the waveguide 2020, such as a distal end of the waveguide 2020 as the distal end cuts or advances through tissue. Such sensed pressures or forces are monitored by the control system and used to determine and control appropriate velocities and/or directions of movement of the robotic arm, which can include either the tool assembly or end effector.

The control system can determine one or more aspects of movement (e.g., direction, velocity, etc.) of the robotic arm based on either a force sensed by the sensor assembly 2000 or a velocity sensed by a sensor. In some embodiments, the velocity of the robotic arm can be determined based on an angular velocity of the motor controlling the velocity or movement of the robotic arm. For example, the motor angular velocity can be determined by motor encoder pulses over time. The control system can control the velocity of movement (e.g., jackhammering) of the robotic arm based on either a sensed force or a sensed velocity. In addition, the control system can control the advancement of the robotic arm in a direction (e.g., toward tissue to be or being cut) based on either the sensed force or the sensed velocity. For example, as the robotic arm is advanced and thereby causing the cutting tool to advance and cut through tissue, the amount of force sensed by the sensor assembly 2000 is used by the control system to determine an appropriate velocity to advance the cutting tool, including when to stop advancement of the cutting tool. Once the cutting tool has cut through the tissue, for example, the force applied to the distal end of the cutting tool is less than when the cutting tool was cutting through tissue, which is sensed by the sensor assembly 2000 and detected by the control system. The control system uses this information, for example, to reduce the velocity of the robotic arm and prevent the cutting tool from undesired cutting of adjacent tissue.

Figure 14:
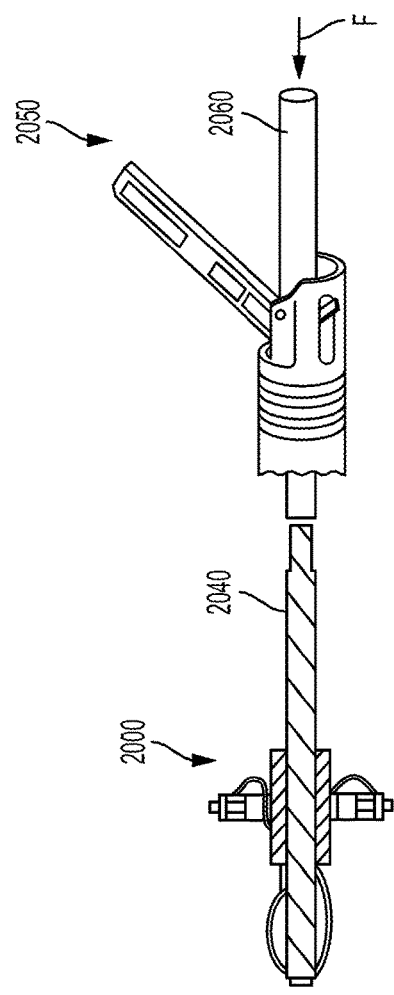
FIG. 14 illustrates the sensor assembly of FIG. 13 coupled to a shaft of the tool assembly and showing an end effector having a cutting tool.

FIG. 14 illustrates the sensor assembly 2000 coupled adjacent to an embodiment of an end effector 2050 that includes a cutting tool 2060 (e.g., tissue boring tool). As shown in FIG. 14, the sensor assembly 2000 is coupled to a part of a shaft 2040 with the end effector 2050 at a distal end of the shaft 2040. Forces applied to a distal end of the cutting tool 2060 are sensed in the shaft 2040 by the sensor assembly 2000. The shaft 2040 and end effector 2050 can be part of a tool assembly coupled to a robotic arm of a robotic surgical system, with the sensor assembly 2000 in communication with the control system. As such, the control system can control the movement of the robotic arm and thus the cutting tool 2060 to perform a cutting or boring of tissue using the cutting tool 2060. As shown in FIG. 14, the cutting tool 2060 (which can be an ultrasonic wave guide) has an elongated cylindrical body that is configured to bore into tissue, such as by jackhammering a distal end of the elongated cylindrical body against and through tissue to puncture or cut through the tissue. Although the cutting tool 2060 is shown in FIG. 14 as having an elongated cylindrical body, the cutting tool 2060 can have any number of various shapes and features for cutting, puncturing, or making an incision in tissue without departing from the scope of this disclosure.

Figure 15B:
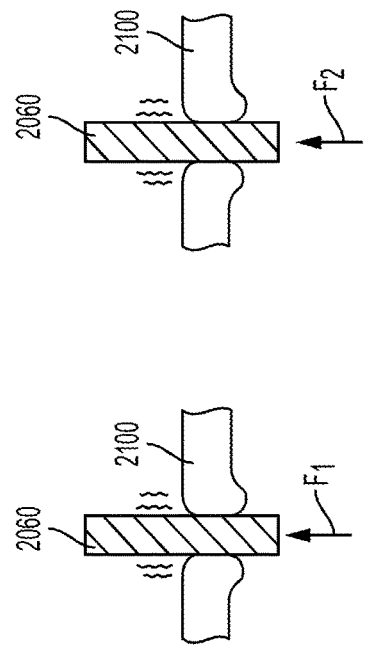
FIG. 15B illustrates the distal end of the cutting tool of FIG. 15A boring through the tissue.
Figure 15C:
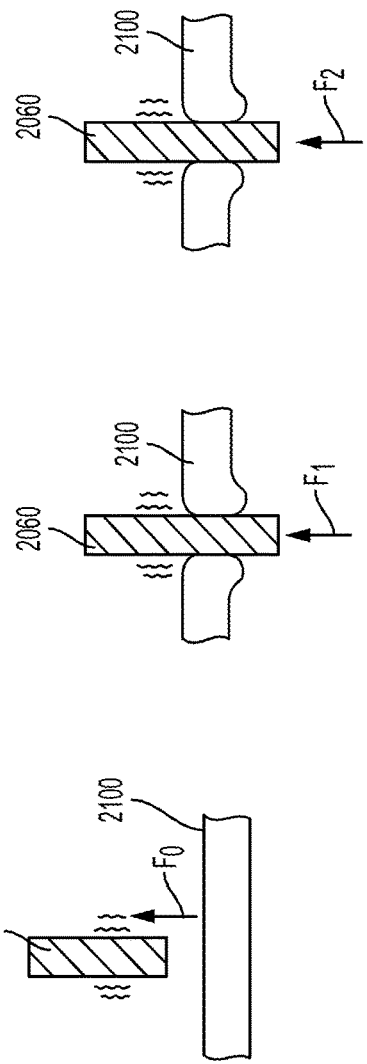
FIG. 15C illustrates the distal end of the cutting tool of FIG. 15B extending through the tissue.

FIGS. 15A-15C illustrate an example of the cutting tool 2060 boring through tissue 2100. As shown in FIG. 15A, the distal end of the cutting tool 2060 is not in contact with the tissue 2100 and therefore a force is not applied against the distal end of the cutting tool 2060 by the tissue 2100. The control system can detect the absence of the applied force to commence or increase the advancement of the robotic arm in the direction of the tissue 2100 to assist with cutting into the tissue 2100. As shown in FIG. 15B, the distal end of the cutting tool 2060 is in contact with the tissue 2100 and a force is applied against the distal end of the cutting tool 2060 by the tissue 2100. A variety of forces can be applied to the distal end of the cutting tool 2060 as the cutting tool 2060 advances through the tissue, which can be monitored by the control system for determining appropriate velocities of movement of the robotic arm (e.g., jackhammering velocity, velocity of advancement of cutting tool, etc.). Control of the robotic arm by the control system can be based on such determined appropriate velocities to assist with effectively cutting the tissue 2100. As shown in FIG. 15C, the distal end of the cutting tool 2060 is extending through the tissue 2100 and is no longer in contact with the tissue 2100. As such, a force is not applied against the distal end of the cutting tool 2060 by the tissue 2100. The control system can detect the absence of the applied force to decrease, including stop, the advancement or movement of the robotic arm, which can prevent unwanted cutting or boring of adjacent tissue. As such, the control system can determine appropriate velocities and directions of movement based on current and past sensed forces and velocities.

In some embodiments of the robotic surgical system, the tool assembly includes a force sensor that detects a force applied by the tissue against a part of the end effector, such as a blade or a first jaw. This applied force sensed by the force sensor can be used by the control system to determine a tension in the tissue. From such determination of tissue tension, the control system can control either how fast to advance the robotic arm (e.g., to cut the tissue), to what extent, if at all, to angle the end effector in order to achieve a desired tension in the tissue, as will be described in greater detail below. Other factors associated with the cutting of tissue can be determined and controlled by the control system based off of the applied force sensed by the force sensor, such as degree of jaw closure thereby effecting tissue compression therebetween and/or energy density (e.g., ultrasonic, radio frequency, etc.) applied to the cutting tool (e.g., blade), as will also be discussed in greater detail below.

When the tissue being cut has a tension that is within a desired or optimal tension range, the quality of the cut or incision is improved and surgical times can be shorter. For example, if the tissue does not have enough tension, the tissue can be hard or impossible to cut, thereby prolonging the surgical procedure and possibly harming the patient. However, if the tissue has too much tension, the tissue can be damaged (e.g., tearing of the tissue, etc.). As such, it is desirable that tissue being cut has a tension that is within a desired tension range in order to efficiently and effectively cut the tissue. The degree to which tissue is compressed between a pair of jaws of an end effector can also contribute to how efficiently and effectively tissue is cut.

FIG. 16 illustrates another embodiment of end effector 3000 positioned at a distal end of a shaft 3010 of a tool assembly that is coupled to a robotic arm (such as the tool assemblies and robotic arms shown in FIGS. 2 and 9). The end effector 3000 includes a first jaw 3020 and a second jaw 3030 that are movable between an open position and a closed position, as well as any number of positions therebetween. The first and second jaws 3020, 3030 are configured to releasably capture tissue therebetween, such as when in the closed or at least partially closed position. When captured between the first and second jaws 2020, 2030, the tissue can experience a variety of compressive forces as a result of the first and second jaws 2020, 2030 varying their relative positioning (e.g., more or less closed). In some implementations, compressive forces can be determined by characterizing the system. For example, the output torque of a motor can be determined by correlating voltage, current, and position (encoder determined) to an output velocity, torque, and position. The actual output force, position and velocity of the end effector with respect to velocity, torque, and position can be determined using a correlating equation and/or lookup table. The control system can use such algorithm and data to convert measurable variables, such as position, torque, and/or velocity, to compressive force, jaw position, and/or velocity.

The end effector 3000 further includes a knife blade 3035 that is slidably disposed along a part of the first jaw 3020. For example, the knife blade 3035 can be advanced in a distal direction from a first position to a second position when the tissue is captured between the first and second jaws 3020, 3030 to thereby cut the tissue. Furthermore, one or more types of energy can be delivered to and from the knife blade 3035, such as radio frequency, for assisting with cutting the tissue. The control system (such as the control system 315 in FIG. 1) can detect and monitor such compressive forces to determine and control an appropriate degree of closure of the first and second jaws 3020, 3030 for achieving an appropriate compression (e.g., within a desired compression range) of the tissue captured between the first and second jaws 3020, 3030 thereby assisting with efficiently and effectively cutting the tissue with the knife blade 3035.

FIG. 17A illustrates another embodiment of end effector 4000 positioned at a distal end of the shaft 3010. The end effector 4000 includes an ultrasonic blade 3040 and a moveable upper jaw or clamp 3075 (see, for example, in FIG. 18) that assists with positioning tissue along the ultrasonic blade 3040. The ultrasonic blade 3040 can deliver ultrasonic energy to the tissue for assisting with cutting the tissue. As shown in FIG. 17A, a section of tissue 3045 is positioned along a distal part of the ultrasonic blade 3040 and applying a force against the distal part of the ultrasonic blade 3040. A proximal end of the ultrasonic blade 3040 is shown coupled to a blade extension or waveguide 3050 that extends along a part of the shaft 3010. The blade extension 3050 can be manipulated at a proximal end (such as at the wrist 980 shown in FIG. 7) for assisting with manipulating the ultrasonic blade 3040, such as angling the ultrasonic blade 3040 relative to the tissue being cut. As shown in FIG. 17A, at least one sensor 3060 is positioned along the ultrasonic blade 3040 or blade extension 3050. The sensors 3060 can be configured to measure the forces applied on the ultrasonic blade 3040 by the tissue 3045, such as shown in FIG. 17A. The control system (such as the control system 315 in FIG. 1) can detect and monitor such sensed applied forces to determine and control an appropriate velocity of movement of the robotic arm that is coupled to the tool assembly having the end effector 4000. Such appropriate velocity of movement includes the velocity of movement of the end effector 4000 in a direction that cuts the tissue. The control system controls the robotic arm (and thus the end effector) to move at the determined appropriate velocity to assist with performing a desired cut of the tissue.

FIG. 17B illustrates a cross sectional view of the shaft of FIG. 17A showing at least one sensor 3060 positioned adjacent the ultrasonic blade 3040 or blade extension 3050. As shown in FIG. 17B, more than one sensor 3060 is positioned radially about the perimeter of the blade extension 3050. Such an arrangement allows for detecting of bending in the ultrasonic blade 3040 or blade extension 3050 due to the tissue applying a force along the ultrasonic blade 3040, as shown in FIG. 17A. The control system can collect and analyze sensed data from any of the one or more sensors 3060 for determining a tension in the tissue. The sensors 3060 can include any one of a variety of sensors for detecting tension in the tissue 3045, including a strain gauge.

As discussed above, the control system can determine, based on the collected sensed force data from the sensors 3060, an appropriate velocity at which to move the robotic arm to cut the tissue. Furthermore, the control system can use such collected sensed data to determine and control an angle of the end effector (including either end effector 3000 or 4000), to cause the tension in the tissue to increase or decrease. For example, it can be desirable to lift or angle the ultrasonic blade 3040 of end effector 4000 relative to a surface plane of the tissue to assist with cutting of the tissue. Such lifting or angling can assist with creating a desired or optimal tension in the tissue. Alternatively (or in addition), the control system can use the collected sensed data to determine and control a degree of closure between the first jaw 2020 and the second jaw 3030 of end effector 3000 to cause an increase or decrease in compressive forces experienced by the tissue captured between the first and second jaws 2020, 3030. For example, the first and second jaws 2020, 3030 can be moved to a more open position to decrease the compressive forces or moved to a more closed position to increase the compressive forces.

Figure 18:
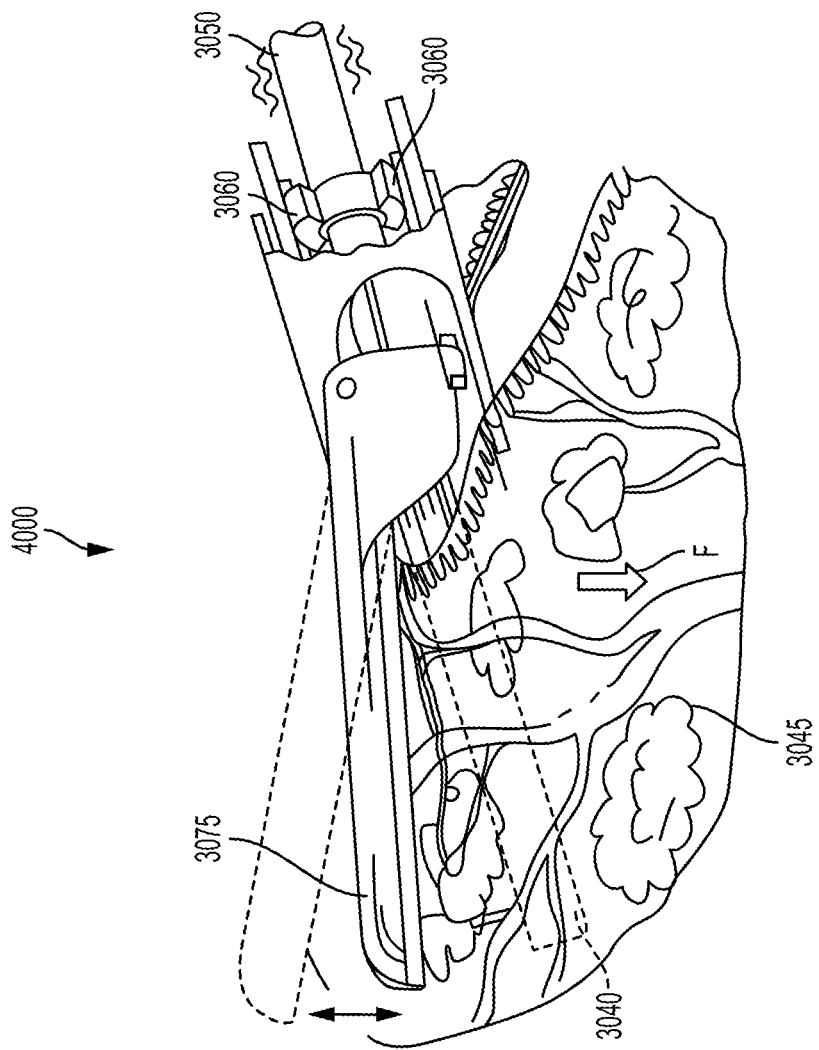
FIG. 18 illustrates the end effector of FIG. 16 being angled relative to the tissue in order to create a desired tension in the tissue.

FIG. 18 illustrates the end effector of FIG. 17A being lifted or angled to cause the force applied by the tissue to increase against the ultrasonic blade 3040 thereby assisting with cutting the tissue 3045 as the end effector 4000 is advanced in a direction that cuts the tissue 3045. Such lifting or angling can be caused by the control system collecting data from the sensors 3060 and determining that the tissue 3045 does not have a tension that is within the desired or optimal tension range. As such, the control system can either adjust the velocity of movement of the robotic arm (including stop movement) in the advancing direction (e.g., to cut tissue) or adjust the orientation of the end effector 4000 relative to the tissue (e.g., angle, lift, and/or lower the end effector 4000). For example, if the control system determines that the tension is too low, the control system can either reduce the velocity of movement of the robotic arm in the advancing direction or move the end effector 4000 such that it is either lifted or angled to create more tension in the tissue 3045. Based on the determined tissue tension, the control system can determine and control an appropriate energy density that is delivered to or received from the ultrasonic blade 3040. For example, if tissue tension is determined to be below a threshold, the velocity of advancement of the robotic arm may be increased. In contrast, stopping or slowing advancement of the robotic arm may further reduce tension. As such, if the tissue tension is above the threshold, the velocity of the robotic arm can be reduced to prevent damage to the tissue. Furthermore, compression applied to the tissue (e.g., via jaw closure) can be increased when the tissue tension is above a threshold and/or additional power can be applied to the tissue to speed up cutting and thereby assist with decreasing tissue tension.

Figure 19:
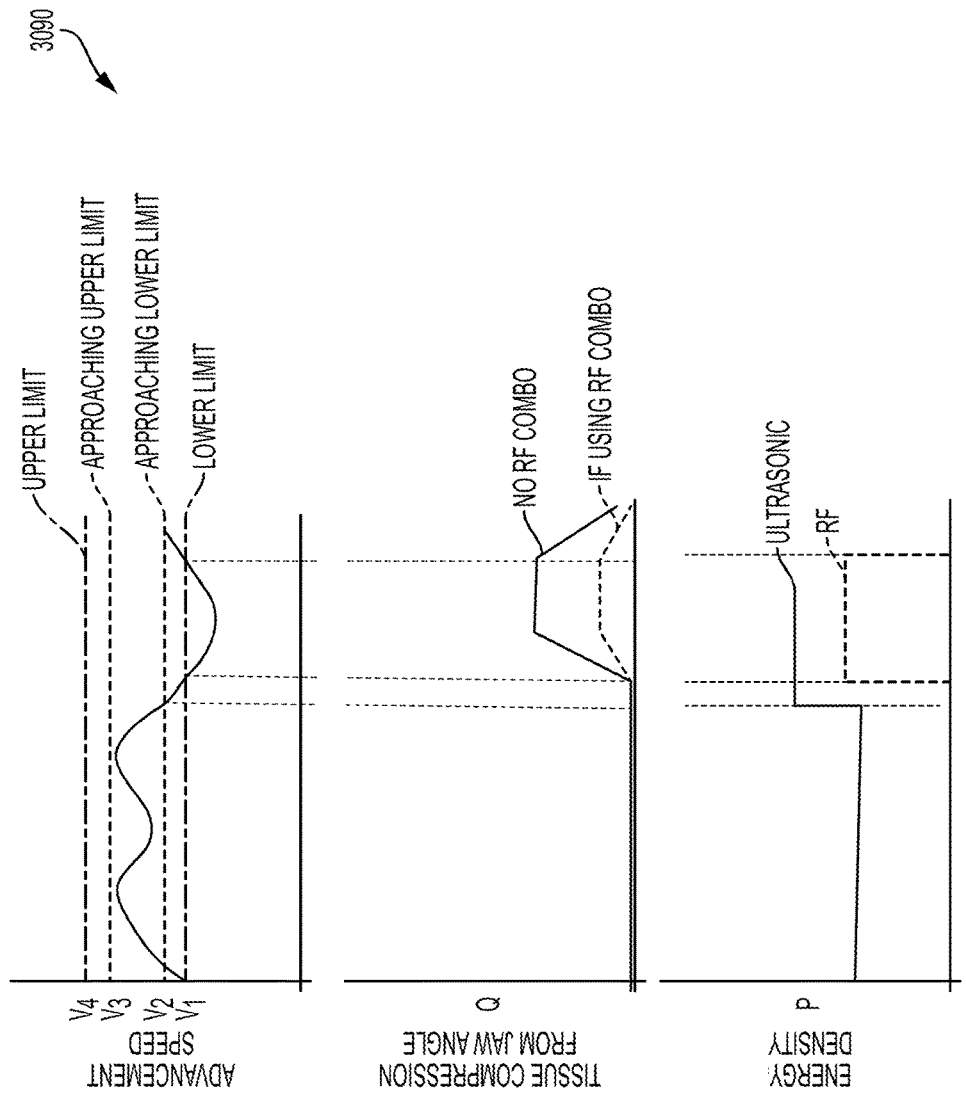
FIG. 19 illustrates a first graph showing exemplary relationships between the advancement speed of the robotic arm or end effector compared to the angle of the end effector relative to the tissue (thereby effecting tissue tension) and energy density in the blade.

FIG. 19 illustrates a first set of graphs 3090 showing exemplary relationships between the advancement speeds of the robotic arm or end effector 4000 compared to the orientation or angle of the end effector 4000 relative to the tissue (thereby affecting either the tissue tension or tissue compression) and energy density in the ultrasonic blade 3040. As shown in FIG. 19, the advancement speed or velocity can be decreased by the control system when the tissue tension is too low and thus requires the end effector to be angled to increase the tissue tension. In addition, during such periods of tissue tension being too low, the energy density can be increased to compensate.

In some implementations of the robotic surgical system, more than one robotic arm can be used to cut or perforate tissue. For example, one surgical arm can be used to detect tension in the tissue to be or being cut. Based on such detected tissue tension, the robotic surgical system can control one or more parameters of a second surgical arm to perform the cutting or perforating of the tissue, as will be discussed in greater detail below.

Figure 20:
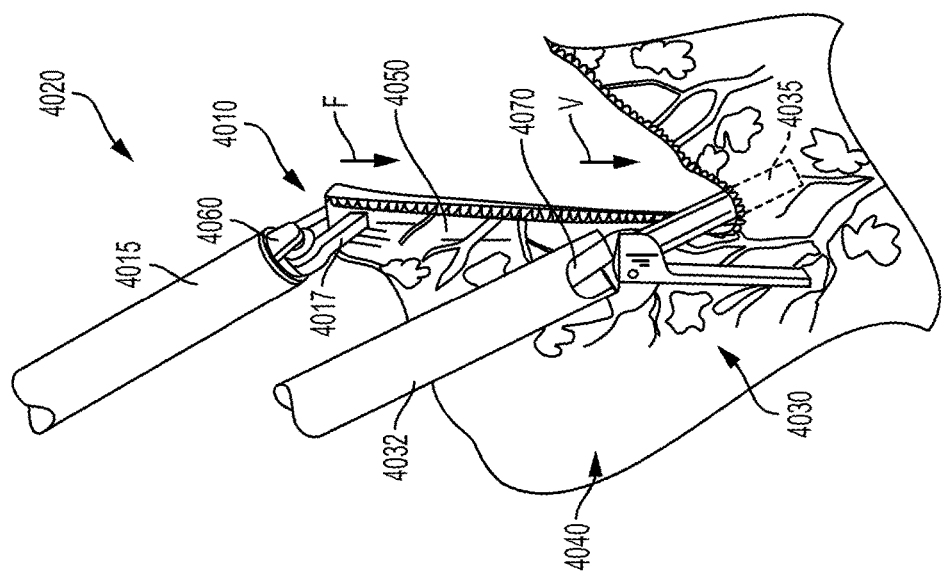
FIG. 20 illustrates an embodiment of a first end effector whose position is controlled by a first robotic arm and includes first and second jaws that are configured to releasably capture tissue therebetween, as well as a second end effector whose position is controlled by a second robotic arm and includes a cutting tool that advances based on a sensed tension detected by a sensor coupled to the first end effector.

FIG. 20 illustrates an embodiment of a first end effector 4010 of a first tool assembly 4020 coupled to a first robotic arm and a second end effector 4030 of a second tool assembly 4040 coupled to a second robotic arm. The first end effector 4010 is coupled to a distal end of a first shaft 4015 of the first tool assembly 4020 and includes a pair of jaws 4017 that are movable between and open and closed configurations. In the closed or partially closed configuration, the pair of jaws 4017 secure a part of tissue 4050 therebetween, as shown in FIG. 20. The pair of jaws 4017 is in communication with a first sensor 4060 that is configured to measure a tension in the tissue 4050 that is partially captured between the pair of jaws 4017. The first sensor 4060 is in communication with a control system of the robotic surgical system (such as the control system 315 of FIG. 1) and the control system can detect and monitor the measurements collected by the first sensor 4060. Based on such measurements, the control system can determine and control one or more of a variety of movement parameters associated with either the first or second robotic arm to effectively and efficiently cut the tissue 4050. The first sensor can include one or more of a variety of sensors, including a strain gauge, and can be positioned in any number of locations along the first end effector 4010 or first tool assembly 4020 for measuring tension in the tissue 4050. For example, any of the tissue tension measuring features and mechanisms discussed above (such as with respects to FIGS. 17A and 17B) can be implemented in this embodiment for measuring tension in the tissue 4050.

As shown in FIG. 20, the second end effector 4030 is positioned at a distal end of a second shaft 4032 of a second tool assembly 4040. The second end effector 4030 includes a cutting tool or blade 4035 that can be advanced into the tissue 4050 for cutting the tissue. The cutting tool 4035 can include any number of features for assisting with cutting tissue, including any of the features discussed above for cutting tissue, such as the blade 3040 shown in FIG. 17A. The cutting tool 4035 is in communication with a second sensor 4070 that is configured to measure an amount of force applied on the cutting tool 4035. The second sensor 4070 is in communication with the control system, which can detect and monitor the applied forces measured by the second sensor 4070. Based on such measured forces, the control system can determine one or more of a variety of movement parameters associated with either the first or second robotic arm to effectively and efficiently cut the tissue 4050. The second sensor 4070 can include one or more of a variety of sensors, including a strain gauge, and can be positioned in any number of locations along the second end effector 4030 or second tool assembly 4040 for measuring the applied forces along the cutting tool 4035. For example, any of the force measuring features and mechanisms discussed above (such as with respects to FIGS. 13 and 17A) can be implemented in this embodiment for measuring a force applied against the cutting tool 4035.

The control system uses the measurements collected from either the first sensor 4060 or the second sensor 4070 to determine and control one or more aspects related to either the first or second robotic arm (including either the first or second end effectors 4010, 4030) to assist with effectively and efficiently cutting the tissue 4050 with the cutting tool 4035. For example, the control system can detect and monitor tissue tension measurements taken from the first sensor 4060 to determine whether the tissue tension is within a desired tension range for cutting. If the tissue tension is not within the desired range, the control system can control the first robotic arm to move such that the first end effector 4010 pulls the tissue in a direction that creates more tension in the tissue. The control system can continue monitoring the tissue tension to determine where to position the first end effector 4010 such that the tissue has a tension that is within the desired range. The control system can also determine, based on the tissue tension, an appropriate speed or velocity at which to advance the cutting tool 4035 to create a cut or incision along the tissue 4050. For example, if the tissue tension is not within the desired tension range, the control system can stop or reduce the velocity of movement of the cutting tool 4035. This can prevent potential damage to the cutting tool 4035 due to the tissue not having sufficient tension to allow the cutting tool 4035 to cut the tissue 4050, as well as prevent damage to the tissue due to cutting tissue having undesired conditions.

Figure 21:
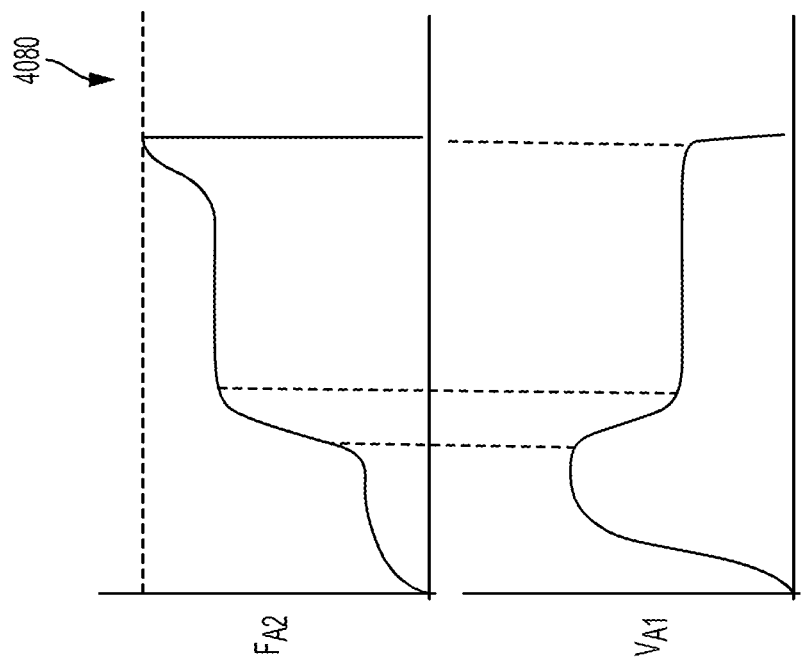
FIG. 21 illustrates a second graph showing an exemplary relationship between the tension sensed in the tissue by the sensor of the first end effector of FIG. 20 and the velocity of movement of the second robotic arm, including the velocity at which the cutting tool advances towards the tissue thereby cutting the tissue.

FIG. 21 illustrates a second graph 4080 showing an exemplary relationship between the tension measured by the first sensor 4060 of the first end effector 4010 and the velocity of movement of the second robotic arm, including the velocity at which the cutting tool 4035 advances and cuts the tissue 4050. As shown in the second graph 4080, the velocity of movement to cut the tissue 4050 can increase as the tension increases to a desired tension range for cutting tissue. When the tension in the tissue becomes increasingly great, the velocity of movement can be reduced and even stopped if the tension becomes too great.

The control system can detect and monitor force measurements taken from the second sensor 4070 to determine whether an appropriate amount of force is being applied against the cutting tool 4035 by the tissue 4050. Based on such measurements, the control system can control the second robotic arm to control the amount of force applied by the tissue 4050 against the cutting tool 4035. For example, the control system can control one or more of a velocity and a direction of movement of the cutting tool 4035 relative to the tissue 4050 being cut. As such, the control system can control either the tension in the tissue 4050 with a first end effector 4010 and a cutting of the tissue 4050 with the second end effector 4030 based off of measurements obtained by either the first or second sensors 4060, 4070. Such a system can allow the robotic surgical system to have simultaneous and independent control of tissue tension and cutting of the tissue.

Figure 22:
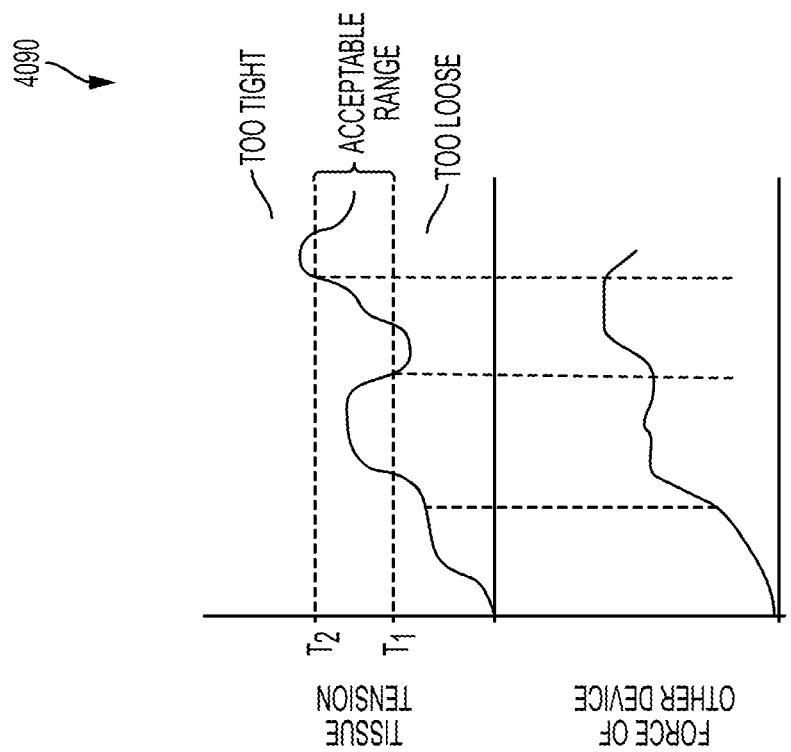
FIG. 22 illustrates a third graph showing an exemplary relationship between the tension sensed in the tissue by the sensor of the first end effector of FIG. 20 and an amount of applied force by the second end effector of the second robotic arm against the tissue.

FIG. 22 illustrates a third graph 4090 showing an exemplary relationship between the tension sensed in the tissue 4050 by the first sensor 4060 and a force applied to the cutting tool 4035 that is sensed by the second sensor 4070. As shown in the third graph 4090, when the tissue 4050 has a tension that is within an acceptable range for cutting the tissue, a greater force can be applied against the cutting tool 4035 by the tissue 4050 for cutting the tissue 4050.

Figure 23:
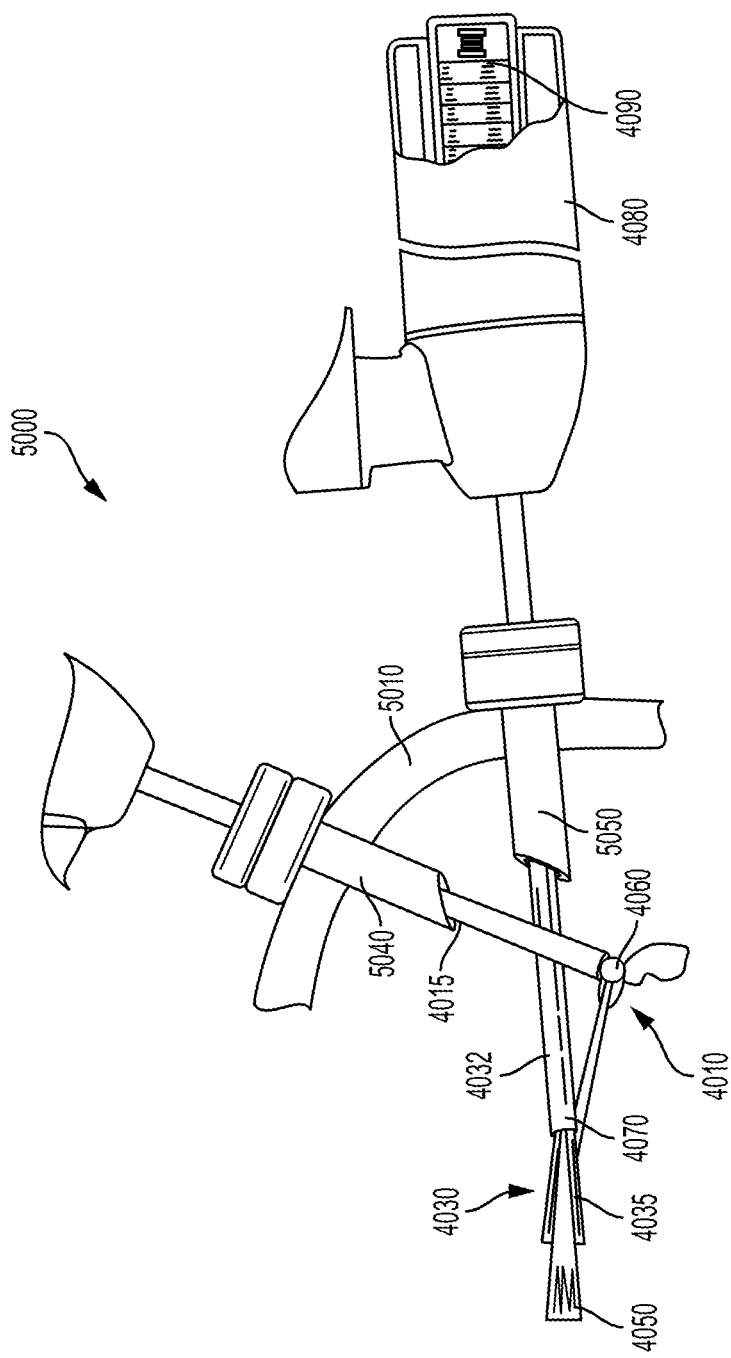
FIG. 23 illustrates an embodiment of a positioning device that secures a positioning of a first shaft of a first tool assembly relative to the second shaft of a second tool assembly.

FIG. 23 illustrates an embodiment of a positioning device 5000 that secures a positioning of the first shaft 4015 of the first tool assembly 4020 relative to the second shaft 4032 of the second tool assembly 4040. For example, the positioning device 5000 includes a radial track 5010 and a first shaft support 5040 and a second shaft support 5050 that is positioned along the radial track to form a variety of orientations (e.g., angles) therebetween. The first shaft support 5040 and the second shaft support 5050 are configured to accept and secure a part of the first shaft 4015 and the second shaft 4032, respectively. As such, the first shaft support 5040 and the second shaft support 5050 can secure the first and second shafts 4015, 4032, respectively, in a variety of orientations (e.g., angles) relative to each other. This can allow for assisting with a variety of procedures, including cutting of the tissue 4050, as shown in FIG. 23.

As shown in FIG. 23, the first end effector positioned at the distal end of the first shaft 4015 can grasp and pull the tissue 4050 for creating a desired amount of tension in the tissue for efficiently and effectively cutting the tissue 4050. The first sensor 4060 associated with the first end effector 4010 can be configured to measure such tissue tension regardless of the orientation of the first and second shafts 4015, 4032. For example, the first sensor 4060 can detect bending in the first shaft 4015, which the control system can use to determine a tension in the tissue 4050. From this determined tissue tension, the control system can control the velocity of advancement of the cutting tool 4035 of the second end effector 4030 to cut the tissue 4050. Any number of sensors can be included in either the first or second tool assemblies 4020, 4040 for detecting any number of forces associated with the tissue or cutting of the tissue, which can be used by the control system for controlling one or more movements and orientations associated with the first and second robotic arms (or the first and second shafts 4015, 4032).

Figure 24:
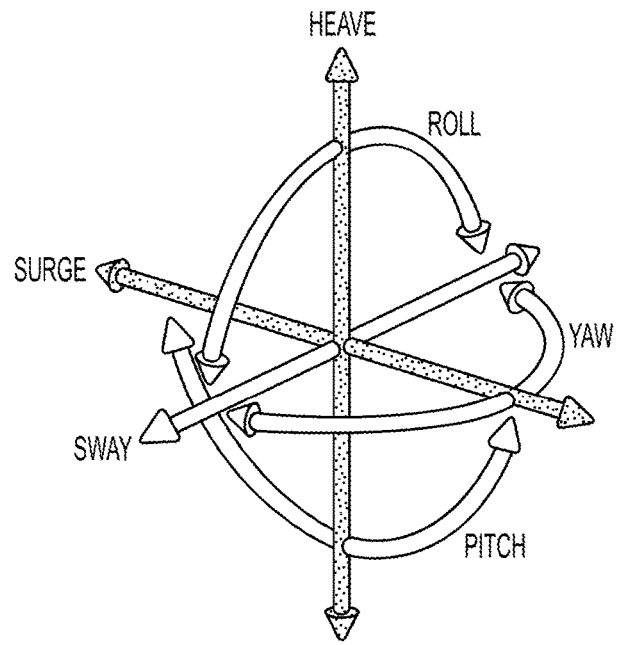
FIG. 24 illustrates movement and rotation along one of the three axes in a Cartesian frame.

There are a number of ways in which to describe the movement of a surgical system, as well as its position and orientation in space. One particularly convenient convention is to characterize a system in terms of its degrees of freedom. The degrees of freedom of a system are the number of independent variables that uniquely identify its pose or configuration. The set of Cartesian degrees of freedom is usually represented by the three translational or position variables, e.g., surge, heave, and sway, and by the three rotational or orientation variables, e.g., Euler angles or roll, pitch, and yaw, that describe the position and orientation of a component of a surgical system with respect to a given reference Cartesian frame. As used herein, and as illustrated in FIG. 24, the term "surge" refers to forward and backward movement, the term "heave" refers to movement up and down, and the term "sway" refers to movement left and right. With regard to the rotational terms, "roll" refers to tilting side to side, "pitch" refers to tilting forward and backward, and "yaw" refers to turning left and right. In a more general sense, each of the translation terms refers to movement along one of the three axes in a Cartesian frame, and each of the rotational terms refers to rotation about one of the three axes in a Cartesian frame.

Although the number of degrees of freedom is at most six, a condition in which all the translational and orientation variables are independently controlled, the number of joint degrees of freedom is generally the result of design choices that involve considerations of the complexity of the mechanism and the task specifications. For non-redundant kinematic chains, the number of independently controlled joints is equal to the degree of mobility for an end effector. For redundant kinematic chains, the end effector will have an equal number of degrees of freedom in Cartesian space that will correspond to a combination of translational and rotational motions. Accordingly, the number of degrees of freedom can be more than, equal to, or less than six.

With regard to characterizing the position of various components of the surgical system and the mechanical frame, the terms "forward" and "rearward" may be used. In general, the term "forward" refers to an end of the surgical system that is closest to the distal end of the input tool, and when in use in a surgical procedure, to the end disposed within a patient's body. The term "rearward" refers to an end of the surgical system farthest from the distal end of the input tool, and when in use, generally to the end farther from the patient.

The terminology used herein is not intended to limit the invention. For example, spatially relative terms, e.g., "superior," "inferior," "beneath," "below," "lower," "above," "upper," "rearward," "forward," etc., may be used to describe one element's or feature's relationship to another element or feature as illustrated in the figures. These spatially relative terms are intended to encompass different positions and orientations of the device in use or operation in addition to the position and orientation shown in the figures. For example, if the device in the figures is turned over, elements described as "inferior to" or "below" other elements or features would then be "superior to" or "above" the other elements or features. Likewise, descriptions of movement along and around various axes include various special device positions and orientations. As will be appreciated by those skilled in the art, specification of the presence of stated features, steps, operations, elements, and/or components does not preclude the presence or addition of one or more other features, steps, operations, elements, components, and/or groups described herein. In addition, components described as coupled may be directly coupled, or they may be indirectly coupled via one or more intermediate components.

There are several general aspects that apply to the various descriptions below. For example, at least one surgical end effector is shown and described in various figures. An end effector is the part of a surgical instrument or assembly that performs a specific surgical function, e.g., forceps/graspers, needle drivers, scissors, electrocautery hooks, staplers, clip appliers/removers, suction tools, irrigation tools, etc. Any end effector can be utilized with the surgical systems described herein. Further, in exemplary embodiments, an end effector can be configured to be manipulated by a user input tool. The input tool can be any tool that allows successful manipulation of the end effector, whether it be a tool similar in shape and style to the end effector, such as an input tool of scissors similar to end effector scissors, or a tool that is different in shape and style to the end effector, such as an input tool of a glove dissimilar to end effector graspers, and such as an input tool of a joystick dissimilar to end effector graspers. In some embodiments, the input tool can be a larger scaled version of the end effector to facilitate ease of use. Such a larger scale input tool can have finger loops or grips of a size suitable for a user to hold. However, the end effector and the input tool can have any relative size.

A slave tool, e.g., a surgical instrument, of the surgical system can be positioned inside a patient's body cavity through an access point in a tissue surface for minimally invasive surgical procedures. Typically, cannulas such as trocars are used to provide a pathway through a tissue surface and/or to prevent a surgical instrument or guide tube from rubbing on patient tissue. Cannulas can be used for both incisions and natural orifices. Some surgical procedures require insufflation, and the cannula can include one or more seals to prevent excess insufflation gas leakage past the instrument or guide tube. In some embodiments, the cannula can have a housing coupled thereto with two or more sealed ports for receiving various types of instruments besides the slave assembly. As will be appreciated by a person skilled in the art, any of the surgical system components disclosed herein can have a functional seal disposed thereon, therein, and/or therearound to prevent and/or reduce insufflation leakage while any portion of the surgical system is disposed through a surgical access port, such as a cannula. The surgical systems can also be used in open surgical procedures. As used herein, a surgical access point is a point at which the slave tool enters a body cavity through a tissue surface, whether through a cannula in a minimally invasive procedure or through an incision in an open procedure.

The systems, devices, and methods disclosed herein can be implemented using one or more computer systems, which may also be referred to herein as digital data processing systems and programmable systems.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computer system may include clients and servers. A client and server are generally remote from each other and typically interact through a communication network. The relationship of client and server arises by virtue of computer programs running on the respective computers and having a client-server relationship to each other.

The computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, e.g., a mouse, a trackball, etc., by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

Figure 25:
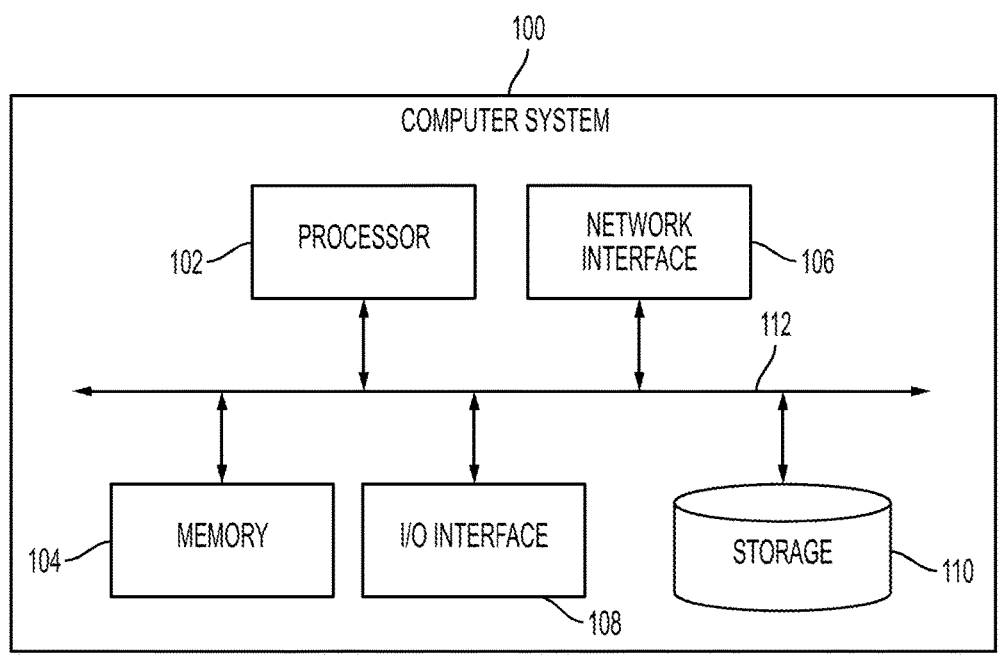
FIG. 25 illustrates an exemplary embodiment of a computer system.

FIG. 25 illustrates one exemplary embodiment of a computer system 100. As shown, the computer system 100 includes one or more processors 102 which can control the operation of the computer system 100. "Processors" are also referred to herein as "controllers." The processor(s) 102 can include any type of microprocessor or central processing unit (CPU), including programmable general-purpose or special-purpose microprocessors and/or any one of a variety of proprietary or commercially available single or multi-processor systems. The computer system 100 can also include one or more memories 104, which can provide temporary storage for code to be executed by the processor(s) 102 or for data acquired from one or more users, storage devices, and/or databases. The memory 104 can include read-only memory (ROM), flash memory, one or more varieties of random access memory (RAM) (e.g., static RAM (SRAM), dynamic RAM (DRAM), or synchronous DRAM (SDRAM)), and/or a combination of memory technologies.

The various elements of the computer system 100 can be coupled to a bus system 112. The illustrated bus system 112 is an abstraction that represents any one or more separate physical busses, communication lines/interfaces, and/or multi-drop or point-to-point connections, connected by appropriate bridges, adapters, and/or controllers. The computer system 100 can also include one or more network interface(s) 106, one or more input/output (TO) interface(s) 108, and one or more storage device(s) 110.

The network interface(s) 106 can enable the computer system 100 to communicate with remote devices, e.g., other computer systems, over a network, and can be, for non-limiting example, remote desktop connection interfaces, Ethernet adapters, and/or other local area network (LAN) adapters. The IO interface(s) 108 can include one or more interface components to connect the computer system 100 with other electronic equipment. For non-limiting example, the IO interface(s) 108 can include high speed data ports, such as universal serial bus (USB) ports, 1394 ports, Wi-Fi, Bluetooth, etc. Additionally, the computer system 100 can be accessible to a human user, and thus the IO interface(s) 108 can include displays, speakers, keyboards, pointing devices, and/or various other video, audio, or alphanumeric interfaces. The storage device(s) 110 can include any conventional medium for storing data in a non-volatile and/or non-transient manner. The storage device(s) 110 can thus hold data and/or instructions in a persistent state, i.e., the value(s) are retained despite interruption of power to the computer system 100. The storage device(s) 110 can include one or more hard disk drives, flash drives, USB drives, optical drives, various media cards, diskettes, compact discs, and/or any combination thereof and can be directly connected to the computer system 100 or remotely connected thereto, such as over a network. In an exemplary embodiment, the storage device(s) can include a tangible or non-transitory computer readable medium configured to store data, e.g., a hard disk drive, a flash drive, a USB drive, an optical drive, a media card, a diskette, a compact disc, etc.

The elements illustrated in FIG. 25 can be some or all of the elements of a single physical machine. In addition, not all of the illustrated elements need to be located on or in the same physical machine. Exemplary computer systems include conventional desktop computers, workstations, minicomputers, laptop computers, tablet computers, personal digital assistants (PDAs), mobile phones, and the like.

The computer system 100 can include a web browser for retrieving web pages or other markup language streams, presenting those pages and/or streams (visually, aurally, or otherwise), executing scripts, controls and other code on those pages/streams, accepting user input with respect to those pages/streams (e.g., for purposes of completing input fields), issuing HyperText Transfer Protocol (HTTP) requests with respect to those pages/streams or otherwise (e.g., for submitting to a server information from the completed input fields), and so forth. The web pages or other markup language can be in HyperText Markup Language (HTML) or other conventional forms, including embedded Extensible Markup Language (XML), scripts, controls, and so forth. The computer system 100 can also include a web server for generating and/or delivering the web pages to client computer systems.

In an exemplary embodiment, the computer system 100 can be provided as a single unit, e.g., as a single server, as a single tower, contained within a single housing, etc. The single unit can be modular such that various aspects thereof can be swapped in and out as needed for, e.g., upgrade, replacement, maintenance, etc., without interrupting functionality of any other aspects of the system. The single unit can thus also be scalable with the ability to be added to as additional modules and/or additional functionality of existing modules are desired and/or improved upon.

A computer system can also include any of a variety of other software and/or hardware components, including by way of non-limiting example, operating systems and database management systems. Although an exemplary computer system is depicted and described herein, it will be appreciated that this is for sake of generality and convenience. In other embodiments, the computer system may differ in architecture and operation from that shown and described here.

The devices disclosed herein can also be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, components of the invention described herein will be processed before use. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high energy electrons. The radiation kills bacteria on the instrument and in the container. The sterilized instrument can then be stored in the sterile container. The sealed container keeps the instrument sterile until it is opened in the medical facility.

Typically, the device is sterilized. This can be done by any number of ways known to those skilled in the art including beta or gamma radiation, ethylene oxide, steam, and a liquid bath (e.g., cold soak). An exemplary embodiment of sterilizing a device including internal circuitry is described in more detail in U.S. Pat. Pub. No. 2009/0202387 filed Feb. 8, 2008 and entitled "System And Method Of Sterilizing An Implantable Medical Device." It is preferred that device, if implanted, is hermetically sealed. This can be done by any number of ways known to those skilled in the art.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A robotic surgical system comprising:
   a first robotic arm;
   a first tool assembly coupled to the first robotic arm, the first tool assembly comprising
      a first shaft extending distally from a first housing;
      a first end effector coupled to a first distal end of the first shaft, the first end effector being configured to manipulate a tissue of a patient; and
      a first sensor operatively coupled to the first end effector and configured to sense a first force applied to the first end effector by the tissue;
   a second robotic arm;
   a second tool assembly coupled to the second robotic arm, the second tool assembly comprising
      a second shaft extending distally from a second housing;
      a second end effector coupled to a second distal end of the second shaft, the second end effector being configured to treat the tissue; and
   a control system configured to control, based on the sensed first force applied to the first end effector, a velocity of movement of the second end effector.

2. The robotic surgical system of claim 1, wherein the second end effector includes a cutting tool that is configured to cut the tissue.

3. The robotic surgical system of claim 2, wherein the second tool assembly further comprises a second sensor that is configured to sense a second force applied to the second end effector in contact with tissue.

4. The robotic surgical system of claim 3, wherein the second force applied to the second end effector by the tissue be tissue tension and the control system is further configured to control, based on at least one of the sensed tissue tension and the sensed second force applied to the second end effector, the velocity of movement of the second end effector relative to the tissue to thereby control the second force applied to the second end effector.

5. The robotic surgical system of claim 2, wherein the cutting tool includes a blade.

6. The robotic surgical system of claim 2, wherein the cutting tool is configured to deliver one or more of an ultrasonic energy and a radio frequency energy to the tissue for assisting with cutting the tissue.

7. The robotic surgical system of claim 1, wherein the control system is further configured to control, based on the sensed first force, a positioning of the first arm to thereby increase or decrease the first force, wherein the first force is tissue tension.

8. The robotic surgical system of claim 1, wherein the first end effector includes a pair of jaws that are configured to grasp the tissue.

9. The robotic surgical system of claim 1, wherein the robotic surgical system further comprises a positioning device that controls an orientation between the first shaft and the second shaft.

10. The robotic surgical system of claim 9, wherein the positioning device includes a first support that releasably secures the first shaft and a second support that releasably secures the second shaft.

11. The robotic surgical system of claim 10, wherein at least one of the first support and the second support are movable along a radial track of the positioning device.

12. The robotic surgical system of claim 1, wherein the first sensor and a second sensor include a strain gauge.

13. The robotic surgical system of claim 1, wherein the movement of the second end effector is affected by movement of at least one of the second robotic arm, the second tool assembly independent of the second robotic arm, and the second end effector independent of at least one of the second robotic arm and the second tool assembly.

14. A method comprising:
   securing a part of a tissue of a patient to a first end effector of a first tool assembly coupled to a first robotic arm of a robotic surgical system;
   sensing, with a first sensor operatively coupled to the first end effector, a tension in the tissue;
   controlling, based on the sensed tension, a velocity of movement of a second tool assembly coupled to a second robotic arm of the robotic surgical system.

15. The method of claim 14, further comprising
   sensing, with a second sensor operatively coupled to a second end effector of the second tool assembly coupled to the second robotic arm, a force applied to a cutting tool of the second end effector; and controlling, based on the sensed force, the velocity of movement of the second tool assembly to thereby cause the sensed force to be within a desired force range.

16. The method of claim 14, further comprising controlling, based on the sensed tension in the tissue, a positioning of the first robotic arm to thereby cause the tension in the tissue to be within a desired tension range.

17. The method of claim 14, wherein the velocity of movement includes a velocity at which a cutting tool cuts the tissue.

18. The method of claim 14, wherein the tissue creates an applied force against a cutting tool.

19. The method of claim 14, wherein the first sensor and a second sensor include a strain gauge.

* * * * *